United States Patent [19]
Harman et al.

[11] Patent Number: 6,020,540
[45] Date of Patent: *Feb. 1, 2000

[54] GENE ENCODING ENDOCHITINASE

[75] Inventors: Gary E. Harman, Geneva, N.Y.; Arne Tronsmo, Aas, Norway; Christopher K. Hayes, Geneva, N.Y.; Matteo Lorito, Salerno, Italy; Sonja Klemsdahl, Ås, Norway

[73] Assignee: Cornell Research Foundation, Inc., Ithaca, N.Y.

[*] Notice: This patent is subject to a terminal disclaimer.

[21] Appl. No.: 08/371,680

[22] Filed: Dec. 21, 1994

Related U.S. Application Data

[63] Continuation-in-part of application No. 08/045,269, Apr. 14, 1993, Pat. No. 5,378,821, and application No. 08/184,115, Jan. 21, 1994, abandoned, said application No. 08/045,269, is a continuation-in-part of application No. 07/919,784, Jul. 27, 1992, which is a continuation-in-part of application No. 07/716,134, Jun. 17, 1991, Pat. No. 5,173,419, said application No. 08/184,115, is a continuation-in-part of application No. 08/049,390, Apr. 21, 1993, Pat. No. 5,474,926, which is a continuation-in-part of application No. 07/990,609, Dec. 15, 1992, Pat. No. 5,326,561.

[51] Int. Cl.$^7$ .............................. C12N 15/56; C12N 5/10; C12N 15/63; A01H 5/00
[52] U.S. Cl. ................. 800/302; 536/23.1; 536/23.2; 435/209; 435/320.1; 435/252.3; 435/418; 435/419
[58] Field of Search .................. 536/23.1, 23.2; 435/209, 320.1, 252.3, 418, 419; 800/302

[56] References Cited

U.S. PATENT DOCUMENTS

| | | | |
|---|---|---|---|
| 4,477,433 | 10/1984 | Hultman | 435/254 |
| 4,489,161 | 12/1984 | Papavisas | 435/254 |
| 4,686,185 | 8/1987 | Wakunaga et al. | 435/206 |
| 4,751,081 | 6/1988 | Suslow et al. | 424/93 |
| 4,940,840 | 7/1990 | Suslow et al. | 435/172.3 X |
| 5,137,819 | 8/1992 | Kilburn et al. | 435/179 |
| 5,168,064 | 12/1992 | Bennett et al. | 435/320.1 |
| 5,173,419 | 12/1992 | Harman et al. | 435/209 |
| 5,187,262 | 2/1993 | Raikhel et al. | 530/370 |
| 5,188,961 | 2/1993 | Overbye et al. | 435/252.31 |
| 5,202,247 | 4/1993 | Kilburn et al. | 435/195 |
| 5,238,843 | 8/1993 | Carpenter et al. | 435/264 |
| 5,258,502 | 11/1993 | Kuranda | 530/350 |
| 5,290,687 | 3/1994 | Suslow et al. | 435/69.1 |
| 5,328,999 | 7/1994 | Bennett et al. | 536/24.5 |
| 5,340,731 | 8/1994 | Kilburn et al. | 435/179 |
| 5,348,743 | 9/1994 | Ryals et al. | 424/94.61 |
| 5,350,689 | 9/1994 | Shillito et al. | 435/240.47 |
| 5,352,607 | 10/1994 | Laine et al. | 435/252.33 |
| 5,356,803 | 10/1994 | Carpenter et al. | 435/200 |
| 5,378,821 | 1/1995 | Harman et al. | 536/23.2 |

FOREIGN PATENT DOCUMENTS

| | | |
|---|---|---|
| 418695 | 3/1991 | European Pat. Off. . |
| 425016 A2 | 5/1991 | European Pat. Off. . |
| 462065 A2 | 12/1991 | European Pat. Off. . |
| 531218 A1 | 3/1993 | European Pat. Off. . |
| 4117026 | 11/1992 | Germany . |
| 88/123645 | 11/1989 | Japan . |
| 2-286082 | 11/1990 | Japan . |
| 5084087 | 4/1993 | Japan . |
| 6046849 | 2/1994 | Japan . |
| WO 90/03732 | 4/1990 | WIPO . |
| WO 92/01792 | 2/1992 | WIPO . |
| WO 94/13784 | 6/1994 | WIPO . |
| WO 94/17667 | 8/1994 | WIPO . |
| WO 94/24271 | 10/1994 | WIPO . |

OTHER PUBLICATIONS

Faure–Raynaud, M., "Determination of the Chitinolytic Activity of Abies Alba Mill. Litter Microorganisms: Bacteria and Yeasts," *Ann. Microbiol.*, 132:267–279 (1981).

Harpster et al., "Relative Strengths of the 35S Califlower Mosaic Virus, 1',2', and Nopaline Synthase Promoters in Transformed Tobacco Sugarbeet and Oilseed Rape Callus Tissue," *Mol Gen Genet*, 212:182–190 (1988).

Gaynor, John J., "Primary Structure of An Endochitinase mRNA From *Solanum tubersum*," *Nucleic Acids Research*, 16:5210 (1988).

Metraux et al., "Isolation of a Complementary DNA Encoding a Chitinase With Structural Homology To a Bifunctional Lysozyme/Chitinase," *Proc. Natl. Acad. Sci. USA*, 86:896–900 (1989).

Harpster et al., "Nucleotide Sequence of the Chitinase B Gene of *Serratia marcescens*," *Nucleic Acids Research*, 17:5395 (1989).

Gaynor et al., "Sequence Analysis of a Genomic Clone Encoding An Endochitinase from *Solanum tubersum*," *Nucleic Acids Research*, 17:5855–5856.

Payne et al., "Isolation of Complementary DNA Clones Encoding Pathogenesis–Related Proteins P and Q, Two Acidic Chitinases From Tobacco," *Proc. Natl. Acad. Sci. USA*, 87:98–102 (1990).

Ori et al., A Major Stylar Matrix Polypeptide (sp41) is a Member of the Pathogenesis–Related Proteins Superclass, *The EMBO Journal*, 9:3429–3236 (1990).

Linthorst et al., "Analysis of Gene Families Encoding Acidic and Basic β–1,3–Glucanases of Tobacco," *Proc. Natl. Acad. Sci. USA*, 87:8756–8760 (1990).

Herget et al., "Elicitor–Specific Induction of One Member of the Chitinase Gene Family in *Arachis hypogaea*," *Mol Gen Genet.*, 224:469–476 (1990).

(List continued on next page.)

*Primary Examiner*—Rebecca E. Prouty
*Attorney, Agent, or Firm*—Nixon, Hargrave, Devans & Doyle LLP

[57] ABSTRACT

Two chitinases from *Trichoderma harzianum* P1 (ATCC 74058) show chitin-containing-fungus-inhibiting activity. One is an endochitinase and the other is a chitobiase. Both have molecular weights of 40 kDa and isoelectric points of 3.9. Endochitinases and chitobiases including the two purified from *Trichoderma harzianum* strain P1 demonstrate synergy with each other in antifungal effect. Isolated gene encoding for the endochitinase has the sequence set forth in the Sequence Listing as SEQ ID NO:1.

33 Claims, 8 Drawing Sheets

OTHER PUBLICATIONS

Henrissat, "Weak Sequence Homologies Among Chitinases Detected By Clustering Analysis," *Protein Seq Data Anal.*, 3:523–526 (1990).

Leah et al., "Biochemical and Molecular Characterization of Three Barley Seed Proteins with Antifungal Properties," *The Journal of Biological Chemistry*, 266:1564–1573 (1991).

Zhu et al., "Isolation and Characterization of a Rice Gene Encoding a Basic Chitinase," *Mol Gen Genet*, 226:289–296 (1991).

De Bolle et al., "A Technique For Detecting Antifungal Activity of Proteins Separated by Polyacrylamide Gel Electrophoresis," *Electrophoresis*, 12:442–444 (1991).

Friedrich et al., "Pathogenesis–Related Protein 4 is Structurally Homologous To the Carboxy–Terminal Domains of Hevein, Win–1 and Win–2," *Mol Gen Genet*, 230:113–119 (1991).

Neuhaus et al., "A Short C–Terminal Sequence is Necessary and Sufficient For the Targeting of Chitinases to the Plant Vacuole," *Proc. Natl. Acad. Sci. USA*, 88:10362–19366 (1991).

Watanabe et al., "Structure of the Gene Encoding Chitinase D of *Bacillus circulans* WL–12 and Possible Homology of the Enzyme to Other Prokaryotic Chitinases and Class III Plant Chitinases," *Journal of Bacteriology*, 174:408–414 (1992).

Verburg et al., "Identification of an Essential Tyrosine Residue in the Catalytic Site of a Chitinase Isolated from *Zea mays* That Is Selectively Modified During Inactivation with 1–Ethyl–3–(dimethylaminopropyl)–carbodiimide," *The Journal of, Biological Chemistry*, 267:3886–3893 (1992).

van Buuren et al., The Structure and Regulation of Homeologous Tobacco Endochitinase Genes of *Nicotiana sylvestris* and *N. Tomentosiformis* Origin, *Mol Gen Genet*, 232–460–469 (1992).

Hejgaard et al., Antifungal Activity of Chitin–Binding PR–4 Type Proteins From Barley Grain and Stressed Leaf, *FEBS Letters*, 307:389–392 (1992).

Flach et al., "What's New in Chitinase Research?," *Experientia*, 48:701–716 (1992).

Araki et al., "The Complete Amino Acid Sequence of Yam (*Dioscorea japonica*) Chitinase," *The Journal of Biological Chemistry,*, 267:19944–19947 (1992).

Hart et al., "Regulated Inactiviation of Homologous Gene Expression in Transgenic *Nicotiana sylvestris* Plants Containing a Defense–Related Tobacco Chitinase Gene," *Mol Gen Genet*, 235:179–188 (1992).

Ishige et al., "Cloning of a Complementary DNA That Encodes an Acidic Chitinase Which is Induced by Ethylene and Expression of the Corresponding Gene," *Plant Cell Physiol.*, 34:103–111 (1993).

Stintzi et al., "Plant 'Pathogenesis–Related' Proteins and Their Role in Defense Against Pathogens," *Biochimie*, 75:687–706 (1993).

Hart et al., "A 61 bp Enhancer Element of the Tobacco β–1,3–Glucanase B Gene Interacts With One or More Regulated Nuclear Proteins," *Plant Molecular Biology*, 21:121–131 (1993).

Melchers et al., "Extracellular Targeting of the Vacuolar Tobacco Proteins AP24, Chitinase and β–1,3–Glucanase in Transgenic Plants," *Plant Molecular Biology*, 21:583–593 (1993).

Benhamou et al., "Antifungal Effect of Bean Endochitinase on *Rhizoctonia solani*: Ultrastructural Changes and Cytochemical Aspects of Chitin Breakdown," *Canadian Journal of Microbiology*, 39:318–328 (1993).

Sticher et al., "Posttranslational Processing of a New Class of Hydroxyproline–Containing Proteins," *Plant Physiol.*, 101:1239–1247 (1993).

Blaak et al., "Characteristics of An Exochitinase From *Streptomyces olivaceoviridis*, Its Corresponding Gene, Putative Protein Domains and Relationship to Other Chitinases," *Eur. J. Biochem.*, 214:659–669 (1993).

Tsujibo et al., "Site–Directed Mutagenesis of Chitinase From Alteromonas sp. Strain O–7," *Biosci. Biotech. Biochem.*, 57:1396–1397 (1993).

Iseli et al., "The N–Terminal Cysteine–Rich Domain of Tobacco Class I Chitinase Is Essential for Chitin Binding but Not for Catalyti Catalytic or Antifungal Activity," *Plant Physiol.*, 103:221–226 (1993).

Vogelsang et al., "Cloning of a Class III Acidic Chitinase from Chickpea," *Plant Physiol.*, 103:297–298 (1993).

Danhash et al., "Molecular Characterization of Four Chitinase cDNAs Obtained From *Cladosporium fulvum*–Infected Tomato," *Plant Molecular Biology*, 22:1017–1029 (1993).

Watanabe et al., "Identification of Glutamic Acid 204 and Aspartic Acid 200 in Chitinase A1 of *Bacillus circulans* WL–12 as Essential Residues for Chitinase Activity," *The Journal of Biological Chemistry*, 268:18567–18572 (1993).

Smigocki et al., "Cytokinin–Mediated Insect Resistance in Nicotiana plants Transformed With the ipt Gene," *Plant Molecular Biology*, 23:325–335 (1993).

Tsujibo et al., "Cloning and Sequence Analysis of the Gene Encoding a Thermostable Chitinase From *Streptomyces thermoviolaceus* OPC–520," *Gene* , 134:113–117 (1993).

Laflamme et al., "Isolation and Nucleotide Sequence of cDNA Clones Encoding Potato Chitinase Genes," *Plant Molecular Biology*, 13:249–250 (1989).

Shinshi et al., "Structure of a Tobacco Endochitinase Gene: Evidence That Different Chitinase Genes Can Arise by Transposition of Sequences Encoding a Cysteine–Rich Domain," *Plant Molecular Biology*, 14:357–368 (1990).

Memelink et al., "Tobacco Genes Encoding Acidic and Basic Isoforms of Pathogenesis–Realted Proteins Display Different Expression Patterns," *Plant Molecular Biology*, 14:119–126 (1990).

Bednarek et al., "The Barley Lectin Carboxyl–Terminal Propeptide Is a Vacuolar Protein Sorting Determinant in Plants," *The Plant Cell*, 3:1195–1206 (1991).

Neale et al., "Chitinase, β–1,3–Glucanase, Osmotin, and Extensin Are Expressed In Tobacco Explants During Flower Formation," *The Plant Cell*, 2:673–684 (1990).

Nielsen et al., "An Acidic Class III Chitinase in Sugar Beet: Induction by *Cercospora beticola*, Characterization, and Expression in Transgenic Tobacco Plants," *Molecular Plant-–Microbe Interactions*, 6:495–506 (1993).

Meier et al., Spatial and Temporal Accumulation of Defense Gene Transcripts in Bean (*Phaseolus vulgaris*) Leaves in Relation to Bacteria–Induced Hypersensitive Cell Death, *Molecular Plant–Microbe Interactions*, 6:453–466 (1993).

Davis et al., "Populus Chitinase Genes: Structure, Organization, and Similarity of Translated Sequences to Herbaceous Plant Chitinases," *Plant Molecular Biology*, 17:631–639 (1991).

Margis–Pinheiro et al., "Isolation of a Complementary DNA Encoding the Bean PR4 Chitinase: An Acidic Enzyme with An—Amino Terminus–Cysteine–Rich Domain," *Plant Molecular Biology*, 17:243–253 (1991).

Edington et al., "cDNA Cloning and Characterization of a Putative 1,3–β–D–Glucanase Transcript Induced by Fungal Elicitor in Bean Cell Suspension Cultures," *Plant Molecular Biology*, 16:81–94 (1991).

Ohme–Takagi et al., "Structure and Expression of a Tobacco β–1,3–Glucanase Gene," *Plant Molecular Biology*, 15:941–946 (1990).

Payne et al., "Evidence for a Third Structural Class of β–1,3–Glucanase in Tobacco," *Plant Molecular Biology*, 15:797–808 (1990).

Ernst et al., "Ozone–Induced Changes of mRNA Levels of β–1,3–Glucanase, Chitinase and 'Pathogenesis–Related' Protein 1b in Tobacco Plants," *Plant Molecular Biology*, 20:673–682 (1992).

van Kan et al., "Differential Accumulation of mRNAs Encoding Extracellular and Intracellular PR Proteins in Tomato Induced by Virulent and Avirulent Races of *Cladosporium fulvum*," *Plant Molecular Biology*, 20:513–527 (1992).

Neuhaus et al., "The Function of Vacuolar β–1,3–Glucanase Investigated by Antisense Transformation. Susceptibility of Transgenic *Nicotiana sylvestris* Plants to *Cercospora nicotianae* Infection," *Plant Molecular Biology*, 19:803–813 (1992).

Lawton et al., "Acidic and Basic Class III Chitinase mRNA Accumulation in Response to TMV Infection of Tobacco," *Plant Molecular Biology*, 19:735–743 (1992).

Lund et al., "A Plant Signal Sequence Enhaces the Secretion of Bacterial ChiA in Transgenic Tobacco," *Plant Molecular Biology*, 18:47–53 (1992).

Araki et al., "Amino Acid Sequence of the N–Terminal Domain of Yam (*Dioscorea japonica*) Aerial Tuber Acidic Chitinase. Evidence for the Presence of a Wheat Germ agglutinin Domain in Matured Acidic Chitinase from Unstressed Tuber," *Plant Molecular Biology*, 19:351–354 (1992).

Shapira et al., "Control of Plant Diseases by Chitinase Expressed from Cloned DNA in *Escheritoia Col.,*" *Phytopatholy*, 79(11):1246–1249 (1989).

Mauch et al., "Antifungal Hydrolases in Pea Tissue—II. Inhibition of Fungal Growth By Combinations of Chitinase and β–1,3–Glucanase," *Plant Physiol.*, 89:936–942 (1988).

Ulhoa et al., "Purification and Some Properties of the Extracellular Chitinase Procuded by *Trichoderma harzianum*," *Enzyme Microb. Technol.*, 14:236–240 (1992).

Arroyo–Begovich, "Chitinase from *Neurospora crassa*," *Meth. in Enzymology*, 161:471–474 (1988).

Pedraza–Reyes et al., "Chitinase Activity in Germinating Cells of *Mucor rouxii*," *Antonie Van Leeunenhoek*, 59(3):183:189 (1991).

Pedraza–Reyes et al., "Detection of Nine Chitinase Sepcies in Germinating Cells of *Mucor rouxii*," *Current Microbiology*, 22(1):43–46 (1991).

Ohtakara et al., "Isolation of Chitinase and Chitobiase Produced by Pycnoporus Cinnabarinus and Their Properties," Chemical Abstracts, 95:7597 (1981).

Otakara et al., "Studies on the Chitinolytic Enzymes of Black–koji Mold," *Agr. Biol. Chem.*, 27(6):454–460 (1963).

Yabuki, Derwert Biotechnology Abstracts, 4(15) 85–07729 (1985) (abstract).

Yabuki, Derwert Biotechnology Abstracts, 4(15) 85–07730 (1985) (abstract).

Kitamoto, Y. et al., "Purification and Some Properties of an Exo–β–1,3–glucanase from *Trichoderma harzianum*," *Agric. Biol. Chem.*, 51(12):3385–3386 (1987).

Ridout et al., "Enzyme Activity and Electrophoretic Profile of Extracellular Protein Induced in Trichoderma spp. by Cell Walls of *Rhizoctonia solani*," *Journal of General Microbiology*, 132:2345–2352 (1986).

Tangarone et al., "Purification and Characterization of an Endo–(1,3)–β–D–Glucanase from *Trichoderma longibrachiatum*," *Applied and Environmental Microbiology*, 55:177–184 (1989).

Ulhoa et al., "Purification and Characterization of an Extracellular Chitobiase from *Trichoderma Harzianum*," *Current Microbiology*, 23:285–289 (1991).

Ulhoa et al., "Regulation of Chitinase Synthesis in *Trichoderma harzianum*," *Journal of General Microbiology*, 137:2163–2169 (1991).

Boller et al., "Chitinase from *Phaseolus vulgair* Leaves," Methods in Enzymology, vol. 161, Wood, W.A. et al., eds., 1988, Academic Press, pp. 479–484, 498–501.

Yabuki et al., "Purification and Characterization of Chitinase and Chitobiase Produced by *Aeromonas Hydrophila* Subsp. Anaerogenes A52," *J. Gen. Appl. Microbiology*, 32:25–38 (1986).

Mauch et al., "Antifungal Hydrolases in Pea Tissue," *Plant Physiol.*, 87:325–333 (1988).

VanHoof et al., "A Single β1,3–Glucanase Secreted by the Maize Pathogen *Cochliobolus carbonum* Acts by an Exolytic Mechanism," *Physiological and Molecular Plant Pathology*, 39:259–267 (1991).

Sullivan et al., "The Secretion of N–Acetylglucosaminidase During Germ–tube Formation in *Candida albicans*," *J. Gen. Microbiol.*, 130:2213–2218 (1984).

Daugrois, J.H. et al., "Purification and Characterization of Two Basic β–1,3–Glucanases Induced in *Colletotrichum lindemuthianum*–Infected Bean Seedlings," *Arch. Biochem. Biophys.*, 292:468–474 (1992).

Zikakis, J.P. et al., "Chitinase–Chitobiase from Soybeam Seeds and Puffballs," in Methods in Enzymology, vol. 161, Wood, W.A. et al., ed., Academic Press, New York, 1988, pp. 490–497.

Manson et al., "Localization of Chitinolytic Enzymes in Blood of Turbot, *Scophthalmus maximus*, and Their Possible Roles in Defense," *J. Fish Biol.*, 40:919–927 (1992).

Gooday, "Physiology of Microbial Degradation of Chitin and Chitosan," *Biodegradation*, 1:177–190 (1990).

Wessels et al., "Wall Structure Wall Growth and Fungal Morphogenesis," eds., Biochemistry of Cell Walls and Membranes in Fungi, Springer–Verlag, London, 1990, pp. 81–95.

El–Sayed et al., "Chitinolytic Activity and Virulence Associated with Native and Mutant Isolates of an Entomopathogenic Fungus, *Nomuraea rileyi*," *J. of Inverterbrate Pathology*, 54:394–403 (1989).

Ohtakara, A., "Chitinase and β–N–acetylhexosaminidase from *Pycnoporus cinnabarinus*" in Methods in Enzymology, vol. 161, Wood, W.A. et al., ed. Academic Press, New York 1988, pp. 462–470.

Giordani, et al., "Antifungal Action of Carica papaya Latex: Isolation of Fungal Cell Wall Hydrolysing Enzymes," *Mycoses*, 34(11–12):469–477 (1991).

Giordani et al., "Glycosidic Activities of *Candida albicans* After Action of Vegetable Latex Saps (Natural Antifungals) and Isoconazole (Synthetic Antifungals)," *Mycoses*, 34(1–2):67–73 (1991).
Tronsmo, A., Aktuelt fra Statens Fagtjeneste for Landbruket 2, 107–113 (1985).
Sivan, A., et al, J. Gen. Microbiol., vol. 135(3), pp. 675–682, Biosis Abstract.
Tronsmo, A., Norwegian Journal of Agricultural Sciences 3:157–161 (1989).
Sandhu, D. K., et al, Enzyme Microb. Technol., Jan. 1989, vol. 11, pp. 21–25.
Tronsmo, A., Phytopathology 79(10), 1153 (1989).
Usui, T., et al, Carbohydrate Research, 203, 65–77 (1990).
De Vries, O.M. H., et al, J. Gen. Microbiol., vol. 76, pp. 319–330 (1973).
Tronsmo, A., Biological Control 1, 59–62 (Aug. 1991).
Takara Biomedicals Brochure for Chitinase T–1, dated Apr. 1989, (portion translated).
Lorita, M., et al, Phytopathology, 82, No. 2, 245–246, (Feb. 1992).
Takara Biomedicals Brochure for β–N–Acetylhexosaminidase from *Trichoderma harzianum* Af6–T8, dated Apr. 1989 (portion translated).
Harman, G. E., et al, Proceedings of EFPP/IOBC Workshop, Copenhagen, Denmark, Jul. 1991.
De La Cruz, J., et al, Eur. J. Biochem. 206, 859–867 (1992).
Lorito, M., et al, Phytopathology, 83, No. 3, 302–307 (1993).
Klemsdal, S. S., et al, 11th Nordic Postgraduate School in Plant Pathology, abstract of poster presented Feb. 3, 1992 in Tisvildeleije, Denmark.
DiPietro, A., et al, Phytopathology, 83, No. 3, 308–312 (1993).
Davies, D.A.L., et al, Nature, vol. 273, May 18, 1978, pp. 235–236.
Microbial Polysaccharides and Polysaccharases, Berkeley, R.C.W., et al, eds., Academic Press, 1979, pp. 285–311, 436–447.
Harman, G. E., et al, Phytopathology, 83, No. 3, 313–318 (1993).
Neuhaus, J.–M., et al, Plant Mol. Biol. 16: 141–151 (1991).
Huynh, J. V., et al, Constructing and screening cDNA libraries in lambda gt10 and lambda gt11, in Glover, D. M., ed., DNA cloning, vol. 1, IRL Press, Washington, DC (1984), pp. 49–78.
Roberts, W. K., et al, J. Gen. Microbiol. 134, 169–176 (1988).
Brogle, K., et al, Science, vol. 254, 1194–1197 (1991).
Oppenheim, A. B., et al, Trends in Biotechnology, vol. 10, No. 11, 392–394 (Nov. 1992).
Belyavsky, A., et al, Nucleic Acids Research 17(8), 2919–2932 (Apr. 1989).
Blaiseau, P.–L., et al, Gene 120, 243–248 (1992).
Berher, S. L, et al, eds., Methods in Enzymology, vol. 152, Guide to Molecular Cloning Techniques, pp. 393–399, 415–423, 432–447, 661–704, Academic Press (1987).
Deutscher, M. P., editor, Methods in Enzymology, vol. 182, Guide to Protein Purification, pp. 602–613, 738–751, Academic Press (1990).
von Bodman, S., et al, Proc. Natl. Acad Sci USA, 83,9443–9447 (Dec. 1986).
Carsolio, C., et al, Proc. Natl. Acad Sci USA 91,10903–10907 (Nov. 1994).
Hayes, C.K., et al, Gene 138, 143–148 (1994).

Kuranda, M.J., et al, J. Biol. Chem. 226, No. 29,19758–19767 Nov. 15, 1991.
Garcia, I., et al, Curr. Genet, 27, 83–89 (1994).
Hartland et al., "The Linkage of (1–3)–β–Glucan to Chitin During Cell Wall Assembly *Saccharomyces cerevisiae*," *Yeast*, 10:1591–1599 (1994).
Lorito et al., "Potential of Genes and Gene Products from Trichoderma sp and Glicladium sp. For the Development of Biological Pesticides," *Molecular Biotechnology*, 2:209–217 (1994).
Perrakis et al., "Crystal Structure of a Bacterial Chitinase At 2.3 Å Resolution," *Current Biology*, 2:1169–1180 (1994).
Samac et al., "Effect of Chitinase Antisense RNA Expression On Disease Susceptibility of Arabidopsis Plants," *Plant Molecular Biology*, 25:587–596 (1994).
Gaffney et al., "Global Regulation of Expression of Antifungal Factors by a *Pseudomonas fluorescens* Biological Control Strain," *Molecular Plant–Microbe Interactions*, 7:455–463 (1994).
Wu et al., "Molecular Analysis of Two cDNA Clones Encoding Acidic Class I Chitinase in Maize," *Plant Physiol.*, 105:1097–1105 (1994).
Clarke et al., "Wound–Induced and Developmental Activation of a Poplar Tree Chitinase Gene Promoter in Transgenic Tobacco," *Plant Molecular Biology*, 25:799–815 (1994).
Koby et al., "The Chitinase Encoding Tn7–Based chiA Gene Endows *Pseudomonas fluorescens* With the Capacity to Control Plant Pathogens In Soil," *Gene*, 147:81–83 (1994).
Brurberg et al., "Expression of a Chitinase Gene From *Serratia marcescens* In *Lactococcus lactis* and *Lactobacillus plantarum*," *Appl Microbiol Biotechnol*, 42:108–115 (1994).
Mylona et al., "The Root Epidermis–Specific Pea Gene RH12 is Homologous To a Pathogenesis–Related Gene," *Plant Molecular Biology*, 26:39–50 (1994).
Leah et al., "Identification of An Enhancer/Silencer Sequence Directing the Aleurone–Specific Expression of a Barley Chitinase Gene Gene," *The Plant Journal*, 6:579–589 (1994).
Heitz et al., "Molecular Characterization of a Novel Tobacco Pathogenesis–Related (PR) Protein: A New Plant Chitinase/Lysozyme," *Mol Gen Genet*, 245:246–254 (1994).
Beerhues et al., "Primary Structure and Expression Of nRNAs Encoding Basic Chitinase and 1,3–β–Glucanase in Potato," *Plant Molecular Biology,*, 24:353–367 (1994).
Ponstein et al., "A Novel Pathogen– and Wound–Inducible Tobacco (*Nicotiana tabacum*) Protein With Antifungal Activity," *Plant Physiol.*, 104:109–118 (1994).
Lawton et al., "Regulation of Cucumber Class III Chitinase Gene Expression," *Molecular Plant–Microbe Interactions*, 7:48–57 (1994).
Yamagami et al., The Complete Amino Acid Sequence of Chitinase–a From the Seeds of Rye (*Secale cereal*), *Biosci. Biotech. Biochem.*, 58:322–329 (1994).
Fukuda et al., "Characterization of a Novel cis–Acting Element That Is Responsive To a Fungal Elicitor In the Promoter of A Tobacc Tobacco Class I Chitinase Gene," *Plant Molecular Biology,*, 24:485–493 (1994).
Holm et al., "Structural Similarity of Plant Chitinase and Lysozymes From Animals and Phage—An Evolutionary Connection," *FEBS Letters*, 340:129–132 (1994).
Staehelin et al., "Perception of Rhizobium Nodulation Factors By Tomato Cells and Inactivation By Root Chitinases," *Proc. Natl. Acad. Sci. USA*, 91:2196–2200 (1994).

Melchers et al., A New Class of Tobacco Chitinases Homologous To Bacterial Exo–Chitinases Displays Antifungal Activity, *The Plant Journal*, 5:469–480 (1994).

Nielsen et al., A Hydroxyproline–Containing Class IV Chitinase of Sugar Beet is Glycosylated With Xylose, *Plant Molecular Biology*, 25:241–257 (1994).

Chet et al., "Biological Control of Fungal Pathogens," *Applied Biochemistry and Biotechnology*, 48:37–43 (1994).

Wemmer et al., The Most Abundant Soluble Basic Protein of the Stylar Transmitting Tract in Potato (*Solanum tubersum* L.) Is An Endochitinase, *Planta*, 194:264–273 (1994).

Neuhaus et al., Mutation Analysis of the C–Terminal Vacuolar Targeting Peptide of Tobacco Chitinase: Low Specificity of the Sortin Sorting System, and Gradula Transition Between Intracellular Retention and Secretion Into the Extracellular Space, *The Plant Journal*, 5:45–54 (1994).

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1554 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 74..1345

(xi) SEQUENCE DESCRIPTION: SEQ ID NO:1:

```
GCTCTTTTCA GCAGCAACTT CTTCCTTTCA AAGCATCTCT TGACAACCTT TGCTGAATCT        60

CAAACACTTC ACC ATG TTG GGC TTC CTC GGA AAA TCC GTG GCC CTG CTT         109
           Met Leu Gly Phe Leu Gly Lys Ser Val Ala Leu Leu
             1               5                  10

GCT GCG CTG CAG GCC ACT CTC ATT TCT GCA TCT CCT GTA ACT GCA AAC        157
Ala Ala Leu Gln Ala Thr Leu Ile Ser Ala Ser Pro Val Thr Ala Asn
             15                  20                  25

GAC GTC TCT GTT GAG AAG AGA GCC AGT GGA TAC GCA AAC GCC GTC TAC        205
Asp Val Ser Val Glu Lys Arg Ala Ser Gly Tyr Ala Asn Ala Val Tyr
       30                  35                  40

TTC ACC AAC TGG GGT ATT TAC GGC CGC AAC TTC CAG CCT CAG AAC CTG        253
Phe Thr Asn Trp Gly Ile Tyr Gly Arg Asn Phe Gln Pro Gln Asn Leu
 45                  50                  55                  60
```

```
                                                        -continued

GTC GCG TCG GAC ATC ACT CAT GTC ATC TAC TCG TTC ATG AAC TTC CAA       301
Val Ala Ser Asp Ile Thr His Val Ile Tyr Ser Phe Met Asn Phe Gln
                    65                  70                  75

GCA GAC GGC ACT GTC GTC TCT GGA GAT GCC TAC GCC GAT TAT CAG AAG       349
Ala Asp Gly Thr Val Val Ser Gly Asp Ala Tyr Ala Asp Tyr Gln Lys
                80                  85                  90

CAC TAT GAC GAC GAT TCT TGG AAC GAC GTC GGT AAC AAT GCG TAC GGC       397
His Tyr Asp Asp Asp Ser Trp Asn Asp Val Gly Asn Asn Ala Tyr Gly
                95                 100                 105

TGT GTG AAG CAG CTG TTC AAG CTG AAG AAG GCC AAC CGC AAC TTG AAG       445
Cys Val Lys Gln Leu Phe Lys Leu Lys Lys Ala Asn Arg Asn Leu Lys
110                 115                 120

GTT ATG CTT TCC ATC GGT GGC TGG ACC TGG TCC ACC AAC TTT CCT TCT       493
Val Met Leu Ser Ile Gly Gly Trp Thr Trp Ser Thr Asn Phe Pro Ser
125                 130                 135                 140

GCA GCA AGC ACC GAT GCC AAC CGC AAG AAC TTT GCC AAG ACT GCC ATC       541
Ala Ala Ser Thr Asp Ala Asn Arg Lys Asn Phe Ala Lys Thr Ala Ile
                145                 150                 155

ACC TTC ATG AAG GAC TGG GGT TTC GAT GGT ATT GAC GTC GAT TGG GAG       589
Thr Phe Met Lys Asp Trp Gly Phe Asp Gly Ile Asp Val Asp Trp Glu
                160                 165                 170

TAC CCC GCC GAT GAT ACC CAG GCC ACC AAC ATG GTT CTT CTG CTC AAG       637
Tyr Pro Ala Asp Asp Thr Gln Ala Thr Asn Met Val Leu Leu Leu Lys
        175                 180                 185

GAG ATC CGA TCT CAG CTA GAT GCC TAT GCT GCG CAA TAC GCT CCG GGC       685
Glu Ile Arg Ser Gln Leu Asp Ala Tyr Ala Ala Gln Tyr Ala Pro Gly
        190                 195                 200

TAC CAC TTC CTT CTT TCC ATT GCT GCC CCC GCT GGC CCA GAG CAC TAC       733
Tyr His Phe Leu Leu Ser Ile Ala Ala Pro Ala Gly Pro Glu His Tyr
205                 210                 215                 220

TCT TTC CTG CAC ATG TCC GAC CTT GGC CAA GTT CTC GAC TAT GTC AAC       781
Ser Phe Leu His Met Ser Asp Leu Gly Gln Val Leu Asp Tyr Val Asn
                225                 230                 235

CTC ATG GCC TAC GAC TAT GCT GGT TCT TGG AGC AGC TAC TCC GGA CAC       829
Leu Met Ala Tyr Asp Tyr Ala Gly Ser Trp Ser Ser Tyr Ser Gly His
            240                 245                 250

GAT GCC AAC TTG TTT GCC AAC CCG TCC AAC CCC AAC TCT TCA CCA TAC       877
Asp Ala Asn Leu Phe Ala Asn Pro Ser Asn Pro Asn Ser Ser Pro Tyr
            255                 260                 265

AAC ACC GAT CAA GCT ATC AAG GAC TAT ATC AAG GGA GGT GTT CCC GCA       925
Asn Thr Asp Gln Ala Ile Lys Asp Tyr Ile Lys Gly Gly Val Pro Ala
270                 275                 280

AGC AAG ATC GTT CTT GGC ATG CCC ATC TAC GGA CGA GCT TTT GAG AGC       973
Ser Lys Ile Val Leu Gly Met Pro Ile Tyr Gly Arg Ala Phe Glu Ser
285                 290                 295                 300

ACC GGT GGC ATT GGC CAG ACC TAC AGT GGA ATT GGA TCT GGA AGC TGG      1021
Thr Gly Gly Ile Gly Gln Thr Tyr Ser Gly Ile Gly Ser Gly Ser Trp
                305                 310                 315

GAG AAC GGT ATT TGG GAC TAC AAG GTT CTT CCC AAG GCC GGC GCC ACA      1069
Glu Asn Gly Ile Trp Asp Tyr Lys Val Leu Pro Lys Ala Gly Ala Thr
            320                 325                 330

GTC CAG TAT GAC TCT GTC GCA CAG GCA TAC TAC AGC TAT GAC CCC AGC      1117
Val Gln Tyr Asp Ser Val Ala Gln Ala Tyr Tyr Ser Tyr Asp Pro Ser
            335                 340                 345

AGC AAG GAG CTC ATC TCT TTC GAT ACC CCT GAC ATG ATC AAC ACC AAG      1165
Ser Lys Glu Leu Ile Ser Phe Asp Thr Pro Asp Met Ile Asn Thr Lys
350                 355                 360

GTC TCT TAC CTC AAG AAC CTC GGC CTG GGA GGC AGC ATG TTC TGG GAA      1213
Val Ser Tyr Leu Lys Asn Leu Gly Leu Gly Gly Ser Met Phe Trp Glu
365                 370                 375                 380
```

```
GCT TCT GCT GAC AAG ACT GGC TCT GAC TCC TTG ATC GGA ACA AGC CAC      1261
Ala Ser Ala Asp Lys Thr Gly Ser Asp Ser Leu Ile Gly Thr Ser His
            385                 390                 395

AGA GCT TTG GGA AGC CTA GAC TCC ACT CAG AAC TTG CTG AGC TAC CCC      1309
Arg Ala Leu Gly Ser Leu Asp Ser Thr Gln Asn Leu Leu Ser Tyr Pro
            400                 405                 410

AAC TCC CAG TAT GAT AAC ATC CGA AGC GGT CTC AAC TAGAGATCTT           1355
Asn Ser Gln Tyr Asp Asn Ile Arg Ser Gly Leu Asn
            415                 420

TCTTCTTCTT ATCTTTTTCT TTTACTTCCC CTATGGTTGT ACCAACATTT CACACACGTT    1415

ATGCGAAACG ATTATGCAGG GAGCGTTATT TTTTAGTAAA TAGTTGCCCT TTGAGATATA    1475

TGAACCTGTA CATAAAGAAC TACTAGCAGT ATATAAGGAG ACATGCAGGA TCTCTAGAAT    1535

TGACTTCCAT GCTTTCCTC                                                  1554

(2) INFORMATION FOR SEQ ID NO:2:

(i) SEQUENCE CHARACTERISTICS:
        (A) LENGTH: 424 amino acids
        (B) TYPE: amino acid
        (D) TOPOLOGY: linear (ii) MOLECULE TYPE: protein (xi) SEQUENCE DESCRIPTION: SEQ ID NO:2:

Met Leu Gly Phe Leu Gly Lys Ser Val Ala Leu Leu Ala Ala Leu Gln
 1               5                  10                  15

Ala Thr Leu Ile Ser Ala Ser Pro Val Thr Ala Asn Asp Val Ser Val
            20                  25                  30

Glu Lys Arg Ala Ser Gly Tyr Ala Asn Ala Val Tyr Phe Thr Asn Trp
            35                  40                  45

Gly Ile Tyr Gly Arg Asn Phe Gln Pro Gln Asn Leu Val Ala Ser Asp
    50                  55                  60

Ile Thr His Val Ile Tyr Ser Phe Met Asn Phe Gln Ala Asp Gly Thr
65              70                  75                  80

Val Val Ser Gly Asp Ala Tyr Ala Asp Tyr Gln Lys His Tyr Asp Asp
                85                  90                  95

Asp Ser Trp Asn Asp Val Gly Asn Asn Ala Tyr Gly Cys Val Lys Gln
            100                 105                 110

Leu Phe Lys Leu Lys Lys Ala Asn Arg Asn Leu Lys Val Met Leu Ser
            115                 120                 125

Ile Gly Gly Trp Thr Trp Ser Thr Asn Phe Pro Ser Ala Ala Ser Thr
    130                 135                 140

Asp Ala Asn Arg Lys Asn Phe Ala Lys Thr Ala Ile Thr Phe Met Lys
145                 150                 155                 160

Asp Trp Gly Phe Asp Gly Ile Asp Val Asp Trp Glu Tyr Pro Ala Asp
                165                 170                 175

Asp Thr Gln Ala Thr Asn Met Val Leu Leu Leu Lys Glu Ile Arg Ser
            180                 185                 190

Gln Leu Asp Ala Tyr Ala Ala Gln Tyr Ala Pro Gly Tyr His Phe Leu
            195                 200                 205

Leu Ser Ile Ala Ala Pro Ala Gly Pro Glu His Tyr Ser Phe Leu His
    210                 215                 220

Met Ser Asp Leu Gly Gln Val Leu Asp Tyr Val Asn Leu Met Ala Tyr
225                 230                 235                 240

Asp Tyr Ala Gly Ser Trp Ser Ser Tyr Ser Gly His Asp Ala Asn Leu
                245                 250                 255
```

```
Phe Ala Asn Pro Ser Asn Pro Asn Ser Ser Pro Tyr Asn Thr Asp Gln
            260                 265                 270

Ala Ile Lys Asp Tyr Ile Lys Gly Gly Val Pro Ala Ser Lys Ile Val
            275                 280                 285

Leu Gly Met Pro Ile Tyr Gly Arg Ala Phe Glu Ser Thr Gly Gly Ile
            290                 295                 300

Gly Gln Thr Tyr Ser Gly Ile Gly Ser Gly Ser Trp Glu Asn Gly Ile
305                 310                 315                 320

Trp Asp Tyr Lys Val Leu Pro Lys Ala Gly Ala Thr Val Gln Tyr Asp
            325                 330                 335

Ser Val Ala Gln Ala Tyr Tyr Ser Tyr Asp Pro Ser Ser Lys Glu Leu
            340                 345                 350

Ile Ser Phe Asp Thr Pro Asp Met Ile Asn Thr Lys Val Ser Tyr Leu
            355                 360                 365

Lys Asn Leu Gly Leu Gly Gly Ser Met Phe Trp Glu Ala Ser Ala Asp
            370                 375                 380

Lys Thr Gly Ser Asp Ser Leu Ile Gly Thr Ser His Arg Ala Leu Gly
385                 390                 395                 400

Ser Leu Asp Ser Thr Gln Asn Leu Leu Ser Tyr Pro Asn Ser Gln Tyr
            405                 410                 415

Asp Asn Ile Arg Ser Gly Leu Asn
            420

(2) INFORMATION FOR SEQ ID NO:3:

(i) SEQUENCE CHARACTERISTICS:
        (A) LENGTH: 1074 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

CAACTTTCCT TCTGCAGCAA GCACCGATGC CAACCGCAAG AACTTTGCCA AGACTGCCAT      60

CACCTTCATG AAGGACTGGG GTTTCGATGG TATTGACGTC GATTGGGAGT ACCCCGCCGA     120

TGATACCCAG GCCACCAACA TGGTTCTTCT GCTCAAGGAG ATCCGATCTC AGCTAGATGC     180

CTATGCTGCG CAATACGCTC CGGGCTACCA CTTCCTTCTT TCCATTGCTG CCCCCGCTGG     240

CCCAGAGCAC TACTCTTTCC TGCACATGTC CGACCTTGGC CAAGTTCTCG ACTATGTCAA     300

CCTCATGGCC TACGACTATG CTGGTTCTTG GAGCAGCTAC TCCGGACACG ATGCCAACTT     360

GTTTGCCAAC CCGTCCAACC CCAACTCTTC ACCATACAAC ACCGATCAAG CTATCAAGGA     420

CTATATCAAG GGAGGTGTTC CCGCAAGCAA GATCGTTCTT GGCATGCCCA TCTACGGACG     480

AGCTTTTGAG AGCACCGGTG GCATTGGCCA GACCTACAGT GGAATTGGAT CTGGAAGCTG     540

GGAGAACGGT ATTTGGGACT ACAAGGTTCT TCCCAAGGCC GGCGCCACAG TCCAGTATGA     600

CTCTGTCGCA CAGGCATACT ACAGCTATGA CCCCAGCAGC AAGGAGCTCA TCTCTTTCGA     660

TACCCCTGAC ATGATCAACA CCAAGGTCTC TTACCTCAAG AACCTCGGCC TGGGAGGCAG     720

CATGTTCTGG GAAGCTTCTG CTGACAAGAC TGGCTCTGAC TCCTTGATCG GAACAAGCCA     780

CAGAGCTTTG GGAAGCCTAG ACTCCACTCA GAACTTGCTG AGCTACCCCA ACTCCCAGTA     840

TGATAACATC CGAAGCGGTC TCAACTAGAG ATCTTTCTTC TTCTTATCTT TTTCTTTTAC     900

TTCCCCTATG GTTGTACCAA CATTTCACAC ACGTTATGCG AAACGATTAT GCAGGGAGCG     960

TTATTTTTTA GTAAATAGTT GCCCTTTGAG ATATATGAAC CTGTACATAA AGAACTACTA    1020
```

```
GCAGTATATA AGGAGACATG CAGGATCTCT AGAATTGACT TCCATGCTTT CCTC          1074
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

```
GTAGCTTTGG GGTCAGGAAG                                                 20
```

(2) INFORMATION FOR SEQ ID NO:5:

(i) SEQUENCE CHARACTERISTICS:
        (A) LENGTH: 628 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
TTGACACCAG ACCAACTGGT AATGGTAGCG ACCGGCGCTC AGCTGGAATT CGCGGCCGCG     60
CTCTTTTCAG CAGCAACTTC TTCCTTTCAA AGCATCTCTT GACAACCTTT GCTGAATCTC    120
AAACACTTCA CCATGTTGGG CTTCCTCGGA AAATCCGTGG CCCTGCTTGC TGCGCTGCAG    180
GCCACTCTCA TTTCTGCATC TCCTGTAACT GCAAACGACG TCTCTGTTGA GAAGAGAGCC    240
AGTGGATACG CAAACGCCGT CTACTTCACC AACTGGGTA TTTACGGCCG CAACTTCCAG     300
CCTCAGAACC TGGTCGCGTC GGACATCACT CATGTCATCT ACTCGTTCAT GAACTTGGAA    360
GCATACGGCA CTGTCGTCTC TGGAGATGCC TACGCCGATT ATCAGAAGCA CTATGACGAC    420
GATTCTTGGA ACGACGTCGG TAACAATGCG TACGGCTGTG TGAAGCAGCT GTTCAAGCTG    480
AAGAAGGCCA ACGGCAACTT GAAGGTTATG CTTTCCATCG GTGGCTGGAC CTGGTCCACC    540
AACTTTCCTT CTGCAGCAAG CACCGATGCC AACCGCAAGA ACTTTGCCAA GACTGCCATC    600
ACCTTCATGA AGGACTGGGG TTTCGATG                                      628
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GCAGGATCTC TAGAATTGAC                                                 20
```

(2) INFORMATION FOR SEQ ID NO:7:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (xi) SEQUENCE DESCRIPTION: SEQ ID NO:7:

```
AAGGTTATGC TTTCCATCGG TGGCTGGACC TGGTCCACCA ACTTT                     45
```

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (xi) SEQUENCE DESCRIPTION: SEQ ID NO:8:

GATGGTATTG ACGTCGATTG GGAGTACCCC                                            30

(2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:9:

Leu Lys Val Met Leu Ser Ile Gly Gly Trp Thr Trp Ser Thr Asn Phe
1               5                   10                  15

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:10:

Asp Gly Ile Asp Val Asp Trp Glu Tyr Pro
1               5                   10

GENE ENCODING ENDOCHITINASE

CROSS-REFERENCE TO RELATED APPLICATION

This is a continuation-in-part of U.S. Ser. No. 08/045,269, filed Apr. 14, 1993, now U.S. Pat. No. 5,378,821, which is a continuation-in-part of U.S. Ser. No. 07/919,784 filed Jul. 27, 1992, which is a continuation-in-part of U.S. Ser. No. 07/716,134, filed Jun. 17, 1991, now U.S. Pat. No. 5,173,419

And a continuation-in-part of U.S. Ser. No. 08/184,115, filed Jan. 21, 1994, now abandoned, which is a continuation-in-part of Ser. No. 08/049,390, filed Apr. 21, 1993, now U.S. Pat. No. 5,474,926, which is a continuation-in-part of U.S. Ser. No. 07/990,609, filed Dec. 15, 1992, now U.S. Pat. No. 5,326,561.

This invention was made in part with Government support under U.S. - Israel International Agricultural Research and Development Fund (BAPD) grant number US-1723-89. The Government has certain rights in the invention.

TECHNICAL FIELD

This invention is directed to isolation of chitinases for biological control of chitin-containing fungi and insects.

BACKGROUND OF THE INVENTION

Application of broad-spectrum pesticides is the primary method used for controlling fungal and insect pests. Such application has resulted in significant environmental pollution and ecological disruption. Pesticide residues are found in food and groundwater and often eliminate beneficial organisms resulting in emergence of secondary pests. Furthermore, as the target pests become less susceptible to the pesticide, there can be a resurgence of the original pest, requiring application of excessive quantities of pesticides for control.

A number of strategies for biological or biorational control of fungal and insect pests have been envisioned. Among the more attractive stratagies are those that target an attribute that is pest specific. One target that has been selected is the structural polymer chitin, which is present in insects and some fungi that attack plants, but is absent in higher plants and vertebrates. U.S. Pat. No. 4,751,081 follows this approach and is directed to novel chitinase-producing bacteria strains for use for inhibiting chitinase-sensitive plant pathogens (fungi and nematodes). The approach of U.S. Pat. No. 4,751,081 lacks flexibility.

SUMMARY OF THE INVENTION

An object of the invention herein is to provide purified chitinases which can be used per se to inhibit fungi and insects that contain chitin or can be used to provide novel chitinase-producing bacteria as in U.S. Pat. No. 4,751,081 or can be used to isolate genes coding for them which can be inserted into a genome of a plant needing protection from a chitin-containing pest.

The chitinases that are the subject of the instant invention are isolated from *Trichoderma harzianum* strain P1. This strain was deposited with the American Type Culture Collection, 12301 Parklawn Drive, Rockville, Md. 20852 on May 20, 1991, under the terms of the Budapest Treaty, and has been assigned accession number ATCC 74058.

The chitinases herein inhibit chitin-containing fungi and insects.

One chitinase herein is an essentially pure protein and has endochitinase activity and has a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 as determined based on its elution profile from a chromatofocusing column. It has a molecular weight of 40 kDa (as determined by sodium dodecyl sulfate polyacrylamide gel electrophoresis after the protein was prepared under reducing conditions, from a regression based on the log of the molecular weight of standard proteins) and an isoelectric point of 3.9 as determined by isoelectric focusing electrophoresis from a regression of distance versus isoelectric point of standard proteins. It has an optimum activity at about pH 4 with a gradual decline to about pH 7. This chitinase is sometimes described hereinafter as the endochitinase herein.

Another chitinase herein has exochitinase activity and has a molecular weight of 36 kDa (as determined by sodium dodecyl sulfate polyacrylamide gel electrophoresis after the protein was prepared under reducing conditions, on direct comparison to migration of 36 kDa protein) and an isoelectric point of 4.4±0.2 as determined based on its elution profile from a chromatofocusing column. It has a molecular weight of 40 kDa (as determined by sodium dodecyl sulfate polyacrylamide gel electrophoresis after the protein was prepared under reducing conditions, from a regression based on the log of the molecular weight of standard proteins) and an isoelectric point of 3.9 as determined by isoelectric focusing electrophoresis from a regression of distance versus isoelectric point of standard proteins. It has chitobiase activity, as indicated by its substrate specificity. It has an optimum activity between pH 4 and pH 7. This chitinase is purified to greater than a 75-fold increase in specific activity compared to its activity in a culture filtrate of *Trichoderma harzianum* strain P1 having accession No. ATCC 74058. This chitinase may be obtained as an essentially pure protein or in purified condition may be present with a minor amount, e.g., up to 40% by weight (total chitobiase basis), of a chitobiase having a molecular weight of 36 kDa (as determined by sodium dodecyl sulfate polyacrylamide gel electrophoresis after the protein was prepared under reducing condition, from regression based on the log of the molecular weight of standard proteins) and an isoelectric point of 3.9 as determined by isoelectric focusing electrophoresis from a regression of distance versus isoelectric point of standard proteins. This chitinase in the form of an essentially pure protein may be described hereinafter as the chitobiase herein.

These chitinases are sometimes referred to collectively hereinafter as the "purified chitinases herein" or as chitinases "of the invention herein".

Where the molecular weight was determined by sodium dodecyl sulfate polyacrylamide gel electrophoresis after the protein was prepared under reducing condition, from regression based on the log of the molecular weight of standard proteins, the proteins were seven standard proteins obtained from Sigma Chemical Co., having molecular weights ranging from 14.2 to 66 kDa, and molecular weights were estimated from a regression equation of the log of molecular weight of the standard proteins versus distance migrated; the seven standard proteins and their molecular weights in kDa are respectively α-lactalbumin, 14.2; soybean trypsin inhibitor, 20.1; trypsinogen, phenylmethylsulfonyl fluoride treated, 24; carbonic anhydrase, 29; glyceraldehyde-3-phosphate, 36; egg albumin, 45; and bovine albumin, 66. When the isoelectric point was determined by isoelectric focusing electrophoresis from a regression of distance versus isoelectric point of standard proteins, comparison was to 12 standard proteins obtained from Pharmacia LKB Biotechnology having isoelectric points ranging from pH 3.5 to pH 9.3; the standard proteins and their isoelectric points are respectively amyloglucosidase, 3.5; methyl red dye, 3.75; soybean trypsin inhibitor, 4.55; β-lactoglobulin, 5.2; bovine carbonic anhydrase B, 5.85; human carbonic anhydrase B, 6.55; horse myoglobin cynocytic band, 6.85; horse myoglobin basic band, 7.35; lentil lectin acidic band, 8.15; lentil lectin middle band, 8.45; lentil lectin basic band, 8.65; and trypsinogen, 9.3. In both cases a linear regression was employed and $r^2$ values ranged from 0.94 to 0.99. For determination of pH optima, 50 mM citric acid and 50 mM of either $K_2HPO_4$ (endochitinase) or $K_3PO_4$ (chitobiase) were prepared and these two solutions were mixed in various ratios to give various pH values and assays were run in triplicate for each pH value and nitrophenyl-β-D-N,N'-diacetylchitobioside and nitrophenyl-β-D-N,N',N"-triacetylchitotriose were used as substrates for chitobiase and endochitinase respectively.

A further embodiment of the invention herein involves a biologically pure (i.e., free of contaminating protein) composition containing endochitinase (enzyme that cleaves chitin randomly) and chitobiase (enzyme that cleaves dimeric units from chitin), preferably the endochitinase herein and the chitobiase herein, in a weight ratio ranging from 3:1 to 1:1.2.

The term "essentially pure" is used herein to mean the presence of a single protein band on a sodium dodecyl sulfate polyacrylamide gel submitted to electrophoresis under reducing conditions and stained with silver stain. The term "in purified condition" means "essentially pure" with exception as stated.

The term "inhibit" is used herein to mean reduce the growth and/or development of fungi or insects compared to where inhibiting agent is not present.

The term "endochitinase activity" is used herein to mean ability to cleave chitin randomly. Such activity is readily determined by an assay to measure reduction of turbidity of a suspension of purified chitin by an agent wherein reduction of turbidity indicates endochitinase activity for the agent. The method of purification of the chitin is described in Vessey, J. C., et al, *Transact. Brit. Mycol. Soc.* 60, 133–143 (1973) and involves grinding and washing crab shell chitin (Sigma Chemical Co.) with distilled water, washing with a mixture containing ethanol:diethyl ether:HCl (50:50:1), bleaching with NaOCl, dissolving in HCl, precipitating by diluting with ice water, and then repeatedly washing with water adjusted to pH 8.5 until the pH of the chitin equals at least 3. The assay involves the following: One g. of purified chitin is suspended in 100 ml 50 mM $KHPO_4$ buffer pH 6.7. To a test tube is added 0.5 ml of this suspension; then 0.5 ml of the test sample is added. The tube is incubated at 30° C. for 24 hours and then diluted with 5 ml water. The optical density of a suspension is determined at 510 nm. The percentage reduction in turbidity is calculated relative to addition of a sample without enzyme.

As used herein, the term "endochitinase" refers to enzymes that randomly cleave chitin.

The term "exochitinase activity" is used herein to mean ability to cleave chitin from one end. Such activity is readily determined by standard assays by release of chromogenic p-nitrophenol from p-nitrophenyl-N-acetyl-β-D-glucosaminide or p-nitrophenyl-β-D-N,N'-diacetylchitobiose, which substrates respectively measure for activity of β-N-acetylglucosaminidase (nagase activity) and N,N'-diacetylchitobiase (chitobiase activity). The assays are the same except for the substrate and involve the following: A substrate solution is formed by dissolving 3 mg of substrate in 10 ml 50 mM $KHPO_4$ buffer pH 6.7. Fifty μl of a substrate solution is added to a well in a microtiter plate (Corning). Thirty μl of test solution is added, and incubation is carried out at 50° C. for 15 minutes. Then the reaction is stopped by addition of 50 μl of 0.4 M $Na_2CO_3$, and the optical density is read at 410 nm. Enzyme solutions may have to be diluted, since optical density readings should be below 1.0. Activity is calculated as the optical density×the dilution factor.

As used herein, the term "chitobiase" means enzyme that cleaves dimeric unit from chitin. Chitobiase is sometimes described herein as "biase." As used herein the term "nagase" means enzyme that cleaves monomeric units from chitin. Both are identified using the enzyme assays described above.

A further aspect of the invention herein involves inhibiting the germination of a chitin-containing fungus which comprises contacting such fungus with an antifungal effective amount of chitinase of the invention herein or of the biologically pure composition herein containing endochitinase and chitobiase. In a preferred use, the fungus is from the genera Fusarium, Botrytis, Trichoderma (different from *Trichoderma harzianum* stain P1), Uncinula or Ustilago.

A further aspect of the invention herein involves the λgtll recombinant containing a cDNA encoding for the endochitinase herein. This λgtll recombinant was deposited with the American Type Culture Collection, 12301 Parklawn Drive, Rockville, Md. 20852 on Jul. 6, 1992, under the terms of the Budapest Treaty as Bacteriophage P1, and has been assigned accession number ATCC 55338.

A further aspect of the invention herein involves the gene encoding for the endochitinase herein removed from the DNA of said λgtll recombinant by the restriction enzyme, Not I.

DETAILED DESCRIPTION

Figure 1:
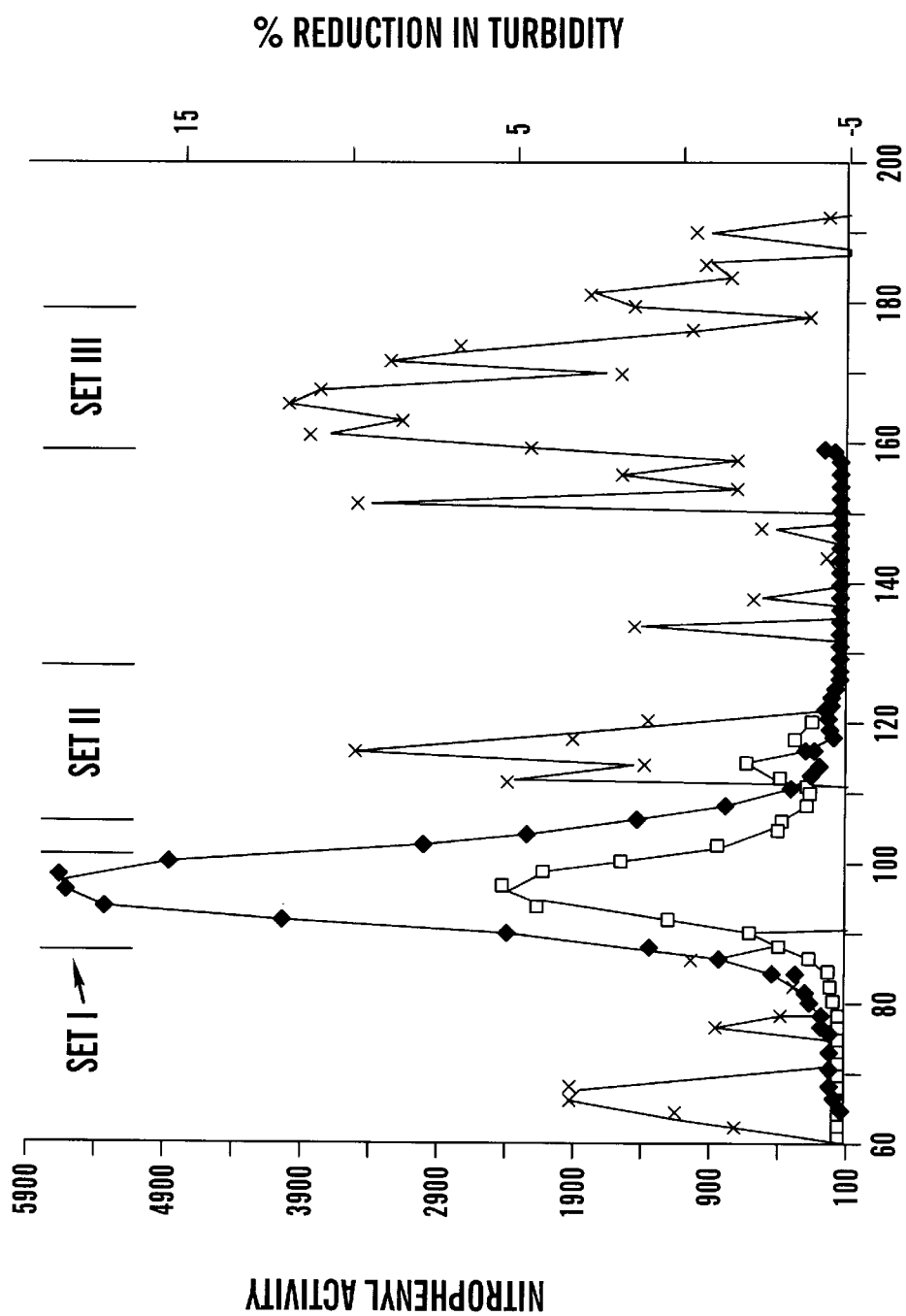
FIG. 1 depicts the elution pattern for the concentrated broth of Example I and provides a graph of endochitinase activity (Fraction vs. % Reduction in Turbidity) denoted by x's, a graph of chitobiase activity (Fraction vs. Nitrophenyl activity) denoted by open boxes, and a graph of nagase activity (Fraction vs. Nitrophenyl activity) denoted by filled-in diamonds.

*Trichoderma harzianum* strain P1 (ATCC 74058) arose as a spontaneously occurring isolate on placement of *Trichoderma harzianum* strain 107 on a medium containing 500 ppm of the fungicide iprodione by inventor A. Tronsmo. Strain 107 was isolated from wood shavings by Dr. C. Dennis in Norfolk, England and was selected by Tronsmo and Dennis as a cold tolerant isolate in a survey for biocontrol agents effective in cold climates. *Trichoderma harzianum* strain P1 (ATCC 74058) has been evaluated as a biocontrol agent as described in Tronsmo, A., *Norwegian Journal of Agricultural Sciences,* 3, 157–161, 1989 (biological control of storage rot on carrots) and has been successfully used as a biocontrol agent of *Botrytis cinerea*, a fungus affecting strawberries, grapes and apples as described in Tronsmo, A., Biological Control, 1, 59–62, 1991 and Harman, G. and Tronsmo, A., unpublished.

The purified protein chitinases herein are obtained from *Trichoderma harzianum* strain P1 (ATCC 74058) as follows: The strain is readily cultured, for example, in modified Richard's medium (composition in one liter of water of 10 g $KNO_3$, 5 g $KH_2PO_4$, 13 g $MgSO_4$, 20 mg $FeCl_3$, 10 g crab shell chitin (Sigma Chemicals), 10 g Polyclar AT (an insoluble polyvinylpyrrolidone from GAF Corp) and 150 ml V8 juice (Campbell Soup Company)) at 25° C. After 3 to 5 days of culturing, the hyphal mass is removed to provide a broth which is dialyzed to remove small molecular weight molecules and then concentrated about 30-fold. The concentrated broth is subjected to liquid chromatography to collect a fraction with chitobiase activity with low nagase activity and a fraction with only endochitinase activity. The fractions are concentrated and the proteins are eluted using a chromatofocusing column. The turbidity reducing portion of the endochitinase activity fraction elutes as a single peak as the essentially pure protein having endochitinase activity, a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of molecular weight of standard proteins) and an isoelectric point of 3.9 as determined by isoelectric focusing electrophoresis from a regression of distance versus the isoelectric point of standard proteins. For the other fraction, a chitobiase portion elutes as a single peak at pH 4.3–4.6 (variation between runs). The chitobiase portion is indicated by polyacrylamide gel electrophoresis under non-reducing conditions to contain an intensively staining protein which has chitobiase activity and has a molecular weight of 36 kDa (as determined by sodium dodecyl sulfate polyacrylamide gel electrophoresis after the protein was prepared under reducing conditions, on direct comparison to migration of a 36 kDa protein), and an isoelectric point of 4.4±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of the molecular weight of standard proteins), and an isoelectric point of 3.9 as determined by isoelectric focusing electrophoresis from a regression of distance versus isoelectric point of standard proteins. Chitobiase can be separated from contaminating proteins by isoelectric focusing on a Rotofor apparatus and consists of two proteins of similar isoelectric point. The larger of the two proteins (40 kDa as determined by sodium dodecyl gel electrophoresis, after the protein was prepared under reducing conditions, from a regression based on the log of the molecular weight of standard proteins), stains more intensively following sodium dodecyl sulfate-polyacrylamide gel electrophoresis and is denoted the protein of the major band. The other chitobiase is denoted the protein of the minor band. The protein of the major band can be obtained in pure form (i.e., uncontaminated by protein of the minor band), if the purification proceeds over several weeks or if the chitobiase is dried in a Speedvac vacuum dryer, presumably since the protein of the minor band is degraded over time or during drying in the Speedvac.

As indicated above, a further embodiment of the invention herein involves a biologically pure (i.e., free of contaminating protein) composition containing endochitinase (enzyme that cleaves chitin randomly) and chitobiase (enzyme that cleaves dimeric units from chitin) in a weight ratio ranging from 3:1 to 1:1.2, preferably ranging from 2:1 to 1:1. This composition provides synergistic antifungal effect compared to endochitinase or chitobiase alone and is considered to be a general occurrence, that is to be the case for all endochitinases and all chitobiases. Preferably the endochitinase is the endochitinase herein and the chitobiase is the chitobiase herein.

The purified chitinases herein, and the biologically pure compositions herein containing endochitinase and chitobiase, inhibit chitin-containing fungi and chitin-containing herbivorous insects. The chitin-containing fungi inhibited by the purified chitinases herein include, for example, species from genera including Fusarium, Gliocladium, Rhizoctonia, Trichoderma, Uncinula, Ustilago, Erysiphe, Botrytis, Saccharomyces, Sclerotium, and Alternaria. The chitin-containing herbivorous insects inhibited by the purified chitinases herein include, for example, Lepidoptera including *Trichoplusia ni* (cabbage looper), *Pieris rapae* (imported cabbage worm), corn earworm, gypsy moth, pink boll worm, tobacco bollworm, diamondback moth, codling moth and spruce budworm; Coleoptera including Colorado potato beetle, boll weevil, Mexican bean beetle and corn rootworm; Homoptera including citrus psylla, cotton aphid, peach-potato aphid and California red scale; Thysanoptera, including onion thrips;

Orthoptera including migratory locusts; Hemiptera including rice stink bug; Diptera including Hessian fly and cabbage root fly; Acari including European red mite, citrus red mite and two spotted mite; Siphonoptera including Lucerne flea; Isoptera including harvester termite; and Hymenoptera including leaf cutting ants.

Inhibition of the aforementioned by the purified chitinases herein or biologically pure composition of endochitinase and chitobiase is readily carried out by contacting the fungus or insect with the chitinase or the biologically pure composition.

The purified chitinase or combinations thereof or biologically pure composition as described above can be utilized as a solution in a concentration, for example, of 50 ppm to 1000 ppm enzyme and applied in the form of a spray, or as a solid wherein the chitinase ingredient(s) is (are) present together with an agriculturally acceptable adhesive carrier, e.g., methyl cellulose or gum arabic, and applied as a powder.

Application can be, for example, to the seed, foliage or roots of a plant to be protected from a chitin-containing insect or plant-pathogenic fungus, or the soil surrounding said plant, or to a chitin-containing fungus or insect to be inhibited.

The purified chitinases herein can also be used to isolate genes coding for them. This can be carried out as follows:

Lyophillized mycelium obtained from Trichoderma harzianum P1 (ATCC 74058) is ground into a fine powder and suspended in a lysis buffer. The suspension is treated with oligo dT cellulose resin which absorbs mRNA, which has a polyadenylated (poly A$^+$) sequence at the 3' end. Unbound cellular debris, chromatin DNA, ribosomal RNA, membranes and other molecules are removed by washing the resin. The mRNA is eluted with a low salt buffer and recovered by ethanol precipitation. This procedure yields 20–100 μg of poly A$^+$ mRNA per gram of dried mycelium. An mRNA isolation kit is commercially available (e.g., from Invitrogen of San Diego, Calif.) for this procedure.

Oligo dT primers are added to 10 μg poly A$^+$ mRNA with the first cDNA strand synthesized by adding reverse transcriptase and dNTP's. The mRNA is degraded from the mRNA:cDNA hybrid and the second cDNA strand is synthesized by adding dNTP's, DNA polymerase 1, T4 DNA polymerase and E. coli ligase. Linkers are added to the newly synthesized cDNA molecules and the molecules are ligated into a viral expression vector, e.g., λgt11, to form viral particles containing a cDNA library. Insertion of the linkered cDNA is upstream of the β-galactosidase stop codon. This formation of viral particles containing a cDNA library from the isolated poly A$^+$ mRNA is readily carried out utilizing a commercially available kit (e.g., from Invitrogen). The viral particles express the cDNA coding sequence when placed into E. coli.

E. coli, strain Y1090, is lytically infected with the viral particles. At the appropriate time, the plaque lawn plate is overlain with a coated membrane that stimulates expression of the β-galactosidase gene containing the ligated cDNA molecule. Expressed fusion particles bind to the membrane, which is probed with polyclonal antibodies specific for the chitinase of interest. Detection of those plaques expressing the genes of interest is determined using a colony screening system. Those plaques expressing the genes of interest are isolated.

The polyclonal antibodies used above are formed by injecting 25 μg of purified chitinase weekly into a rabbit, for a total of six injections. Total antibodies are isolated from the rabbit serum (Goding, J. W., Monoclonal Antibodies, Academic Press, London, 1983), with cross-reactivity and specificity determined using Western blots (Burnett, W. N., Anal. Biochem., 112, 195–203 (1981).

The gene (cDNA insert) can be removed from the λgt11 recombinant by using the restriction enzyme, Not I.

The genes produced as above can be inserted into microorganisms by known methods, e.g. as in U.S. Pat. No. 4,751,081. The transgenic microorganisms can be used to produce chitinase or as biocontrol agents.

The genes produced as above can be also inserted by known methods into plants (e.g., as described in European patent application 339,009) as a defense against chitinase-sensitive pests.

The Rotofor apparatus, mentioned above and used in the examples below, is manufactured by Bio Rad and is a free solution isoelectric focusing apparatus for preparative protein purification on the basis of isoelectric point. It consists of a cylindrical horizontal focusing chamber which rotates about its axis to eliminate thermal and gravitational convection and can hold up to 58 ml of solution to be separated. The chamber contains 19 polyester membrane screens arranged in parallel within the focusing chamber. These screens allow the proteins to migrate during focusing but maintain separation patterns until the moment of harvesting. The solution containing the sample to be separated is mixed with an appropriate ampholyte solution, and the admixture is placed evenly in the horizontal apparatus. A current is applied, and the ampholytes migrate to the position where they have a net zero electrical charge, and in this way a pH gradient is formed. The proteins to be separated also migrate to the region containing the pH where they have a net zero charge (i.e., to the pH of their isoelectric point). Once this separation has occurred, separate samples are collected from each of the 20 compartments provided by the 19 polyester membrane screens by a vacuum sampling apparatus.

The invention is illustrated in the following specific examples:

EXAMPLE I

Modified Richard's medium (as described hereinbefore) containing 1% chitin from crab shells as the sole carbon source is placed in ten 250 ml Erlenmeyer flasks (100 ml/flask) and sterilization is carried out by autoclaving. Two ml of a heavy suspension of conidia (approximately $10^9$/ml) of Trichoderma harzianum strain P1 (ATCC 74058) were used to inoculate each flask and the resulting cultures were grown on a rotary shaker for 4 days at 25° C.

After four days of culturing, the hyphal mass was removed from the medium by centrifugation, and the supernatant (800 ml) was dialyzed against 50 mM KHPO$_4$ buffer pH 6.7 (MWCO 8,000) to remove small molecular weight molecules and then concentrated about 30-fold by applying polyethylene glycol (MW 35,000) to the outside of the dialysis tubing, to produce a concentrated broth.

Figure 2:
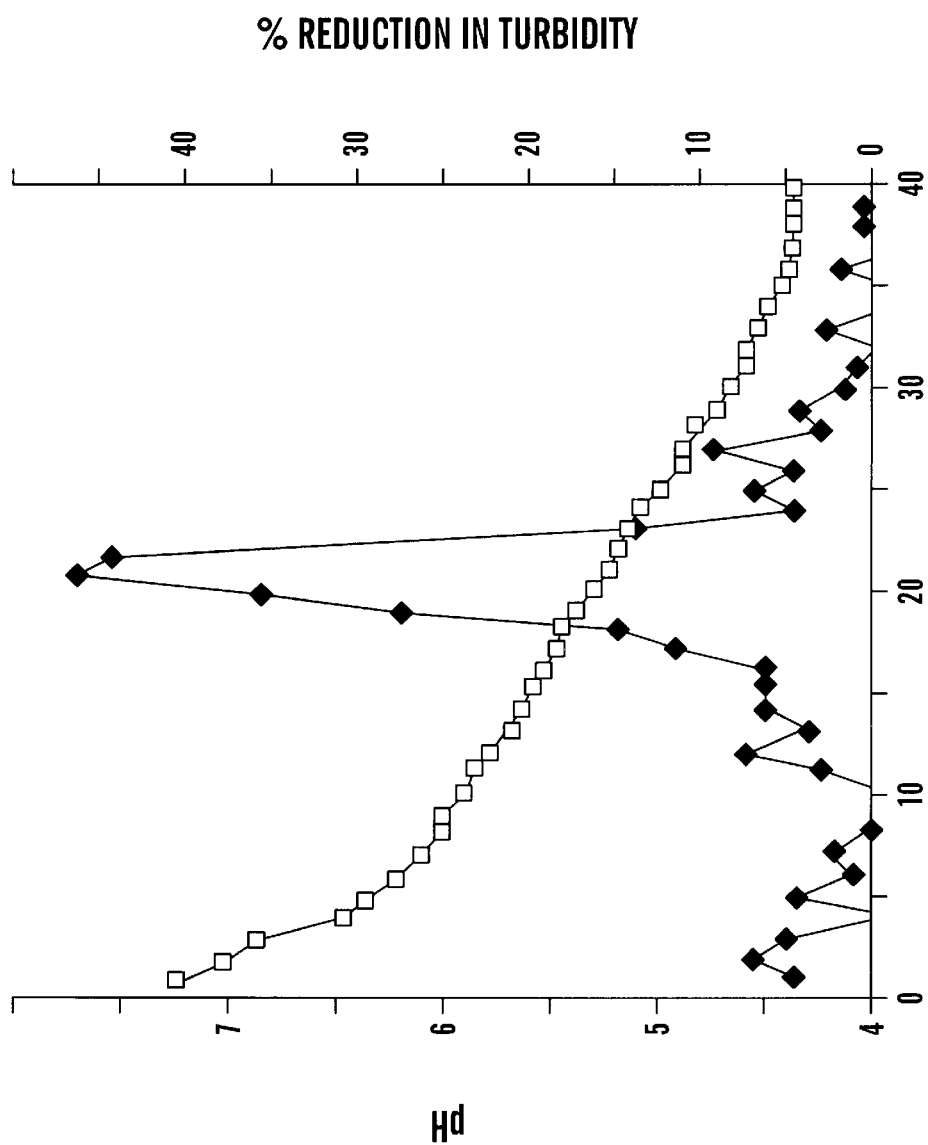
FIG. 2 depicts the elution pattern for concentrated fractions of Set III of Example I and provides a graph of endochitinase activity (Fraction vs. % Reduction in Turbidity) denoted by filled-in diamonds, and a graph of Fraction vs. pH denoted by open boxes.
Figure 3:
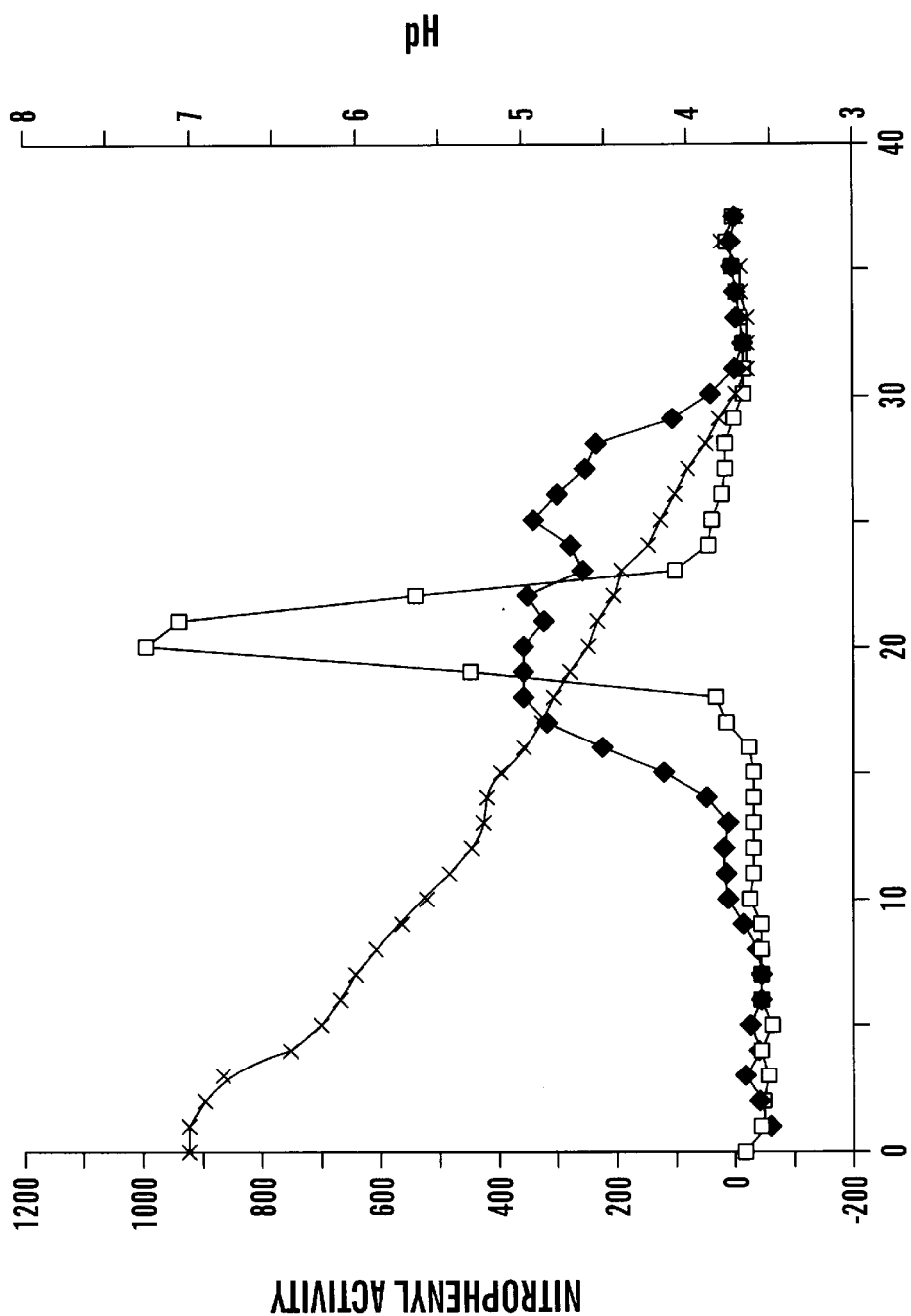
FIG. 3 depicts the elution pattern for concentrated fractions of Set II of Example I and provides a graph of nagase activity (Fraction vs. Nitrophenyl activity) denoted by filled-in diamonds, a graph of chitobiase activity (Fraction vs. Nitrophenyl activity) denoted by open boxes and a peak at fraction 20 and a graph of Fraction vs. pH denoted by x's and having a progressively descending path.

The concentrated broth (approximately 30 ml), in two separate samples, was applied to a 5×60 cm Sephacryl S-300 column and eluted with 50 mM KHPO$_4$ buffer pH 6.7 containing 200 mM NaCl. Each elution fraction consisted of about 8 ml. The elution profiles of enzyme activity are shown in FIG. 1. In FIG. 1, the X's denote the graph for % reduction in turbidity (endochitinase activity), the open boxes denote the graph for biase activity and the filled-in diamonds denote the graph for nagase activity. As shown in FIG. 1, the void volume eluted at fraction 60, and a peak of nagase and biase activity eluted at about fraction 100. At about fraction 115 there was a peak of chitobiase activity and endochitinase activity, but little nagase activity. At fractions 160–180 there was a broad peak containing only endochitinase activity. These fractions were combined into three sets, designated I, II and III, as shown on FIG. 1. Set I (approximately 120 ml) contained nagase and chitobiase activity. Set II (approximately 160 ml) contained chitobiase activity and endochitinase activity and a low level of nagase activity. Set III (approximately 200 ml) contained only endochitinase activity. Set II was combined with a similar fraction from another run on the Sephacryl column. Set III was combined with a similar fraction from another run of the Sephacryl column. The Set II combined fractions were dialyzed against 25 mM imidazole-HCl buffer 6.7 and concentrated to 20 to 60 ml. The Set III combined fractions were dialyzed against 25 mM imidazole-HCl buffer 6.7 and concentrated to 20 to 60 ml. These concentrates were applied to 1.1×25 cm chromatofocusing columns equilibrated with 25 mM imidazole buffer. The proteins were eluted with Polybuffer at a pH range of 6.7 to 4. The elution pattern for the concentrate of combined Sets III is shown in FIG. 2 wherein the open boxes denote the graph for Fraction vs. pH and the filled-in diamonds denote the graph for Fraction vs. % reduction in turbidity. The endochitinase (turbidity reducing) activity from the concentrate of combined Sets III (fraction numbers 20 to 22 consisting of approximately 24 ml) eluted at a single peak at pH 5.3±0.2. The purity of enzyme in this fraction after dialysis and drying was confirmed by polyacrylamide gel electrophoresis under non-denaturing conditions; only a single protein band was detected with silver stain. The protein in this band is determined to have a molecular weight of 36 kDa by sodium dodecyl sulfate polyacrylamide gel electrophoresis after protein was prepared under reducing conditions, on direct comparison to migration of a 36 kDa protein; a molecular weight of 40 kDa by sodium dodecyl sulfate polyacrylamide gel electrophoresis after the protein is prepared under reducing conditions, from a regression based on the log of the molecular weight of standard proteins; an isoelectric point of 5.3±0.2 based on its elution profile from a chromatofocusing column; and an isoelectric point of 3.9 by isoelectric focusing electrophoresis from a regression of distance versus isoelectric point of standard proteins. The elution pattern for the concentrate of combined Sets II is shown in FIG. 3 wherein the graph denoted by filled in diamonds is for nagase activity, the graph denoted by open boxes and a peak at about fraction 20 is for chitobiase activity, and the graph denoted by x's that progresses downwardly is for Fraction vs. pH. As shown in FIG. 3, the fractions with the greatest amount of chitobiase activity (fractions 19–22 consisting approximately of 32 ml) eluted in a single peak at about pH 4.6. In another run these fractions eluted in a single peak at about pH 4.3. As shown in FIG. 3 these fractions contained some nagase activity. This peak (after dialysis and drying) was found by polyacrylamide gel electrophoresis under non-reducing conditions to contain three protein bands. Only one of these bands, the most intensively staining one, was found to have chitobiase activity. The protein of this band was determined to have an isoelectric point of 4.4±0.2 (based on its elution profile from a chromatofocusing column), has an isoelectric point of 3.9 by isoelectric focusing electrophoresis from a regression of distance versus isoelectric point of standard proteins, was determined by sodium dodecyl sulfate polyacrylamide gel electrophoresis after the protein was prepared under reducing conditions to have a molecular weight of about 36 kDa on direct comparison to migration of a 36 kDa protein, and has a molecular weight of 40 kDa by sodium dodecyl sulfate polyacrylamide gel electrophoresis after the protein is prepared under reducing conditions, and the molecular weight determined from regression based on the log of the molecular weight of standard proteins. This protein is isolated from the other two present by gel filtration liquid chromatography on Bio-Gel P-60 (Bio Rad Laboratories).

Comparative Example I

Chitinases isolated from pea, tomato and bean were reported to be endochitinases and to have molecular weights of 27–39 kDa and isoelectric points ranging from 8.87 to 9.4.

An enzyme from *T. reesei* which is an endochitinase was estimated to have a molecular weight of 58 kDa.

The enzyme system of *Serratia marcescens* strain QMB1466 (ATCC 990) was reported to have chitobiase activity. This activity is associated, on sodium dodecyl sulfate polyacrylamide gel electrophoresis under reducing conditions, with two major protein bands of molecular weights at 52.5 and 58 kDa and two minor protein bands of molecular weights of 21.5 and 40.4 kDa. This strain is the one used in the working Example of U.S. Pat. No. 4,751,081 for chitinase activity.

EXAMPLE II

The purified endochitinase from Sets III in Example I (fraction numbers 20 to 22 of FIG. 2) and purified chitobiase enzyme from Sets II in Example I (fraction numbers 19–22 in FIG. 3), that is the fraction containing the essentially pure endochitinase having a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 based on its elution profile from a chromatofocusing column (denoted endochitinase below) and the fraction containing the protein having chitobiase activity, a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 4.4±0.2 as determined based on its elution profile from a chromatofocusing column (denoted biase below), were assayed for antifungal activity against Fusarium sp. and *Trichoderma harzianum* (ATCC 20847). This was carried out on the dialyzed, dried fractions, as follows: A solution containing 500 ppm of enzyme (dialyzed, dried fraction) in distilled water was prepared and was sterilized by filtration through a 0.45 μm filter. From each sterilized composition an assay mixture was prepared that contained 100 μl of the sterilized composition, 100 μl of 3× potato dextrose broth (Difco Laboratories), and 100 μl of a fungal spore suspension ($10^6$/ml). Each assay mixture was incubated. Results of spore germination after a 12 hour incubation were as follows:

TABLE 1

| Enzyme | Organism | Spore Germination % |
| --- | --- | --- |
| None (control) | Fusarium | 85 |
| Biase | Fusarium | 63 |
| Endochitinase | Fusarium | 58 |
| None (control) | Trichoderma | 49 |
| Biase | Trichoderma | 20 |
| Endochitinase | Trichoderma | 22 |

These data show that spore germination was inhibited by the enzyme solutions.

Other effects were noted as follows: Germ tube growth was inhibited after 24 hours of incubation of the Trichoderma strain by both the biase solution and the endochitinase solution. Among spores producing germ tubes, the average length (of 15 measured) for germ tubes germinating in the absence of the enzyme was 198 μm, while the average length of germ tubes in the presence of the biase was 55 μm and the average length of germ tubes in the presence of the endochitinase was 58 μm.

EXAMPLE III

Filter sterilized broth prepared from *Trichoderma harzianum* strain P1 (ATCC 74058) was compared to filter-sterilized broth from *T. virde* 105, *T. koningii* 8, *T. koningii* 417, *T. koningii* VS023, *T. harzianum* 1295-22, and *Gliocladium virens* VS031 as follows: In each case, a diet was made consisting of the following in parts by weight: 57 parts Trichoderma or Gliocladium broth, 11.4 parts wheat germ, 2 parts casein, 1.4 parts agar, 1 part Vitamin Premix (Hoffman-LaRoche #26862), 0.8 parts Wesson Salt Mixture (Bio Serv, Inc.), 0.2 parts sorbic acid, 0.1 parts methyl paraben, and 26 parts distilled water. Larvae of *T. ni* and *P. rapae* were provided with the diet, ad libitum from neonate until the controls reached the ultimate instar, and then all larvae were weighed. Only two of the fungal strains, *G. virens* VS031 and *T. harzianum* P1 (ATCC 74058), reduced the growth of both the larval *T. ni* and *P. rapae* below 60%. The filter-sterilized broth from each of these two strains was dialyzed (MWCO 8,000) to remove small molecular weight molecules and incorporated into the artificial diet as described above. Again, the broth from these two strains significantly reduced the growth of larval *T. ni* and *P. rapae*. The ammonium sulfate precipitable protein in the filter-sterilized, dialyzed broth from both strains was tested for biological activity against larval *T. ni* and *P. rapae* as above. The chitinase activity of the original P1 broth was not precipitated while that of the VS031 broth was. The ammonium sulfate precipitated protein from strain VS031 significantly reduced larval growth while that of strain P1 did not.

EXAMPLE IV

A medium containing 10 g $KNO_3$, 5 g $KH_2PO_4$, 2.5 g $MgSO_4 \times 7H_2O$, 2 mg $FeCl_3$, 10 g crab shell chitin (Sigma Chemical Co.), 150 ml of vegetable juice cocktail (V8 juice), 10 g polyvinylpyrollidone (Polyclar AT, GAF Corp.) and 1000 ml water was adjusted to pH 6 and then sterilized by autoclaving.

The medium was placed in Erlenmeyer flasks (100 ml per 250 ml flask) and each flask was inoculated with a spore suspension of *Trichoderma harzianum* strain P1 (ATCC 74058) to give about $5 \times 10^6$ conidia final concentration and the inoculated flasks were placed on a rotary shaker at 150 RPM at 25° C. for 4 or 5 days. The liquid was separated from the biomass by centrifugation at 8000×g for 10 minutes and residual particulates were removed through a glass fiber filter to provide a culture filtrate containing the enzymes of interest.

The culture filtrate was dialyzed against 50 mM $KPO_4$ buffer pH 6.7 (6 liters of buffer per liter of culture filtrate) overnight at 4° C. with stirring. After dialysis, the dialysis tubes were placed in polyethylene glycol (35,000 MW, Fluka Chemika-Biochemika) until the volume was reduced 15- to 25-fold.

The concentrated culture filtrate (approximately 15 ml) in two separate samples was applied to a 5×60 cm chromatography column packed with Sephacryl S-300 (Pharmacia LKB Biotechnology) equilibrated with 50 mM $KPO_4$ buffer pH 6.7 containing 200 mM NaCl and 0.02% $NaN_3$ and eluted with the same buffer. The concentrated culture filtrate and elution buffer were applied from the bottom of the column using a pump set to deliver 2.3 ml per minute, and fractions were collected every 5 minutes.

Figure 4:
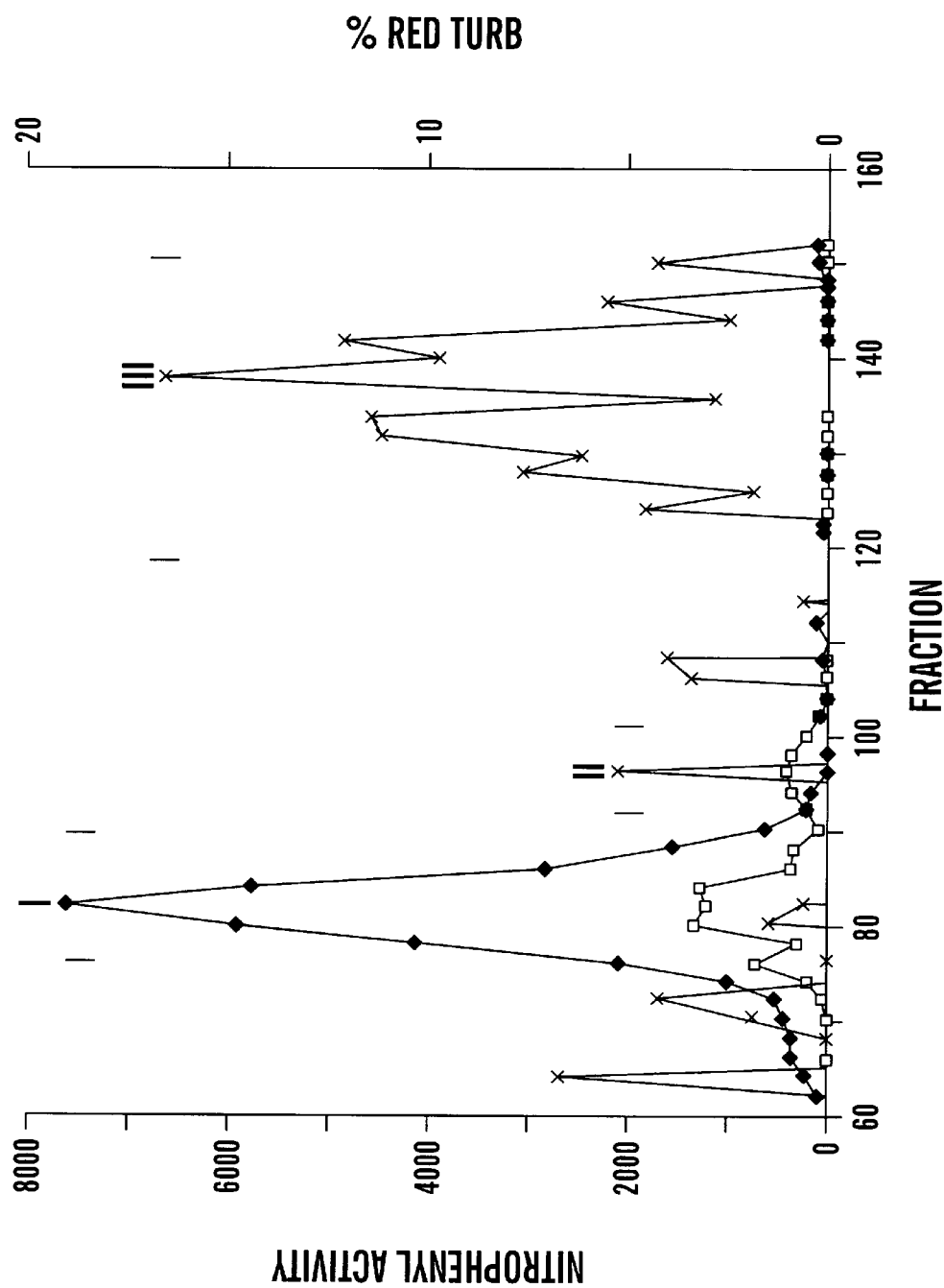
FIG. 4 depicts the elution pattern for the concentrated broth of Example IV and provides a graph of endochitinase activity (Fraction vs. % Red Turbidity, i.e., % Reduction in Turbidity) denoted by x's, a graph of chitobiase activity (Fraction vs. Nitrophenyl activity) denoted by filled in diamonds and a graph of nagase activity (Fraction vs. Nitrophenyl activity) denoted by open squares.

The elution profiles of enzyme activity are shown in FIG. 4. In FIG. 4, the x's denote endochitinase activity, the open boxes denote chitobiase activity and the filled in diamonds denote nagase activity. As shown in FIG. 4, at fractions 92–100 there was a peak of chitobiase activity together with endochitinase and nagase activity; these fractions were designated set II. As shown in FIG. 4, fractions 120–150 contained most of the endochitinase activity; these fractions were designated Set III.

Figure 5:
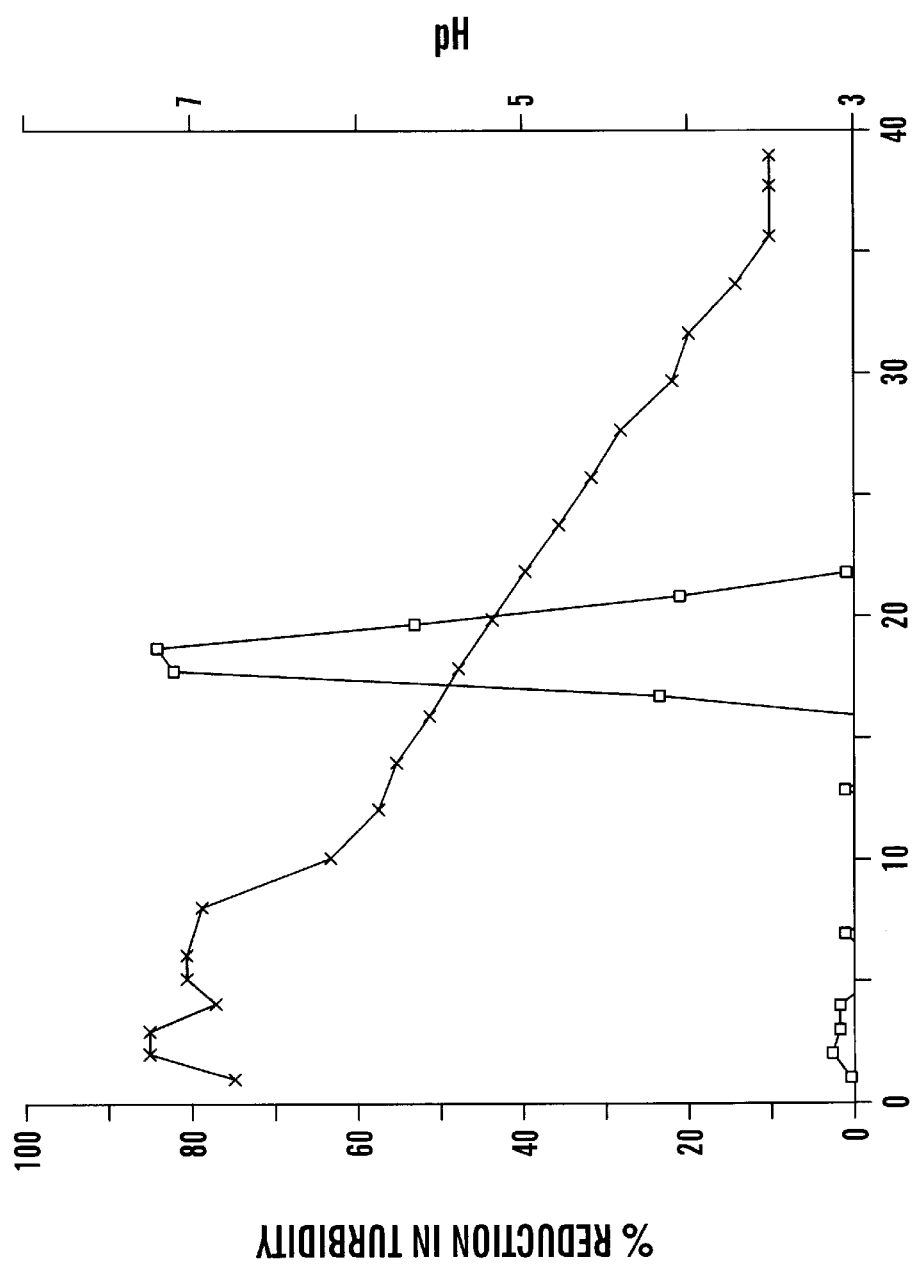
FIG. 5 depicts the elution pattern for the fractions of Set III of Example IV and provides a graph of endochitinase activity (Fraction vs. % Reduction in Turbidity) denoted by open squares, and a graph of Fraction vs. pH denoted by x's.

The fractions of Set III (345 ml) were pooled, and the combined fractions were concentrated to 25 ml in dialysis tubing immersed in polyethylene glycol (molecular weight of 35,000) overnight against approximately a 10-fold volume of 25 mM imidazole-HCl buffer pH 7. The concentrate was applied to a 1×30 cm chromatofocusing column packed with PBE 94 (Pharmacia LKB Biotechnology) equilibrated with 25 mM imidazole buffer. The proteins were eluted with Polybuffer (Pharmacia LKB Biotechnology), at a pH range of 7 to 4. The elution pattern for concentrated fractions of set III is shown in FIG. 5. In FIG. 5, the open boxes denote endochitinase activity and the x's denote pH. Electrophoresis on native, sodium dodecyl sulfate and isoelectric focusing gels showed a single protein. Activity, as determined by fluorescence of methylumbelliferyl substrate, corresponded to the protein band on isoelectric focusing and native gels and showed the protein to be an endochitinase. The molecular weight of the protein was determined to be 40 kDA (as determined by sodium dodecyl sulfate polyacrylamide gel electrophoresis after the protein was prepared under reducing conditions, from a regression based on the log of the molecular weight of standard proteins) and the isoelectric point of the protein was determined to be 3.9 by isoelectric focusing electrophoresis from a regression of distance versus isoelectric point of standard proteins. The specific activity of the purified endochitinase was determined to be 0.86 units/μg protein with the turbidity reducing assay and 2.2 nkat/μg protein when nitrophenyl-$\beta$-D-N,N',N"-triacetylchitotriose was used as the substrate. The specific activity of the endochitinase in the original culture filtrate could not be determined because said filtrate contains an inhibitor of endochitinase activity. The endochitinase was determined to have optimum activity at about pH 4 with a gradual decline to about pH7.

Figure 6:
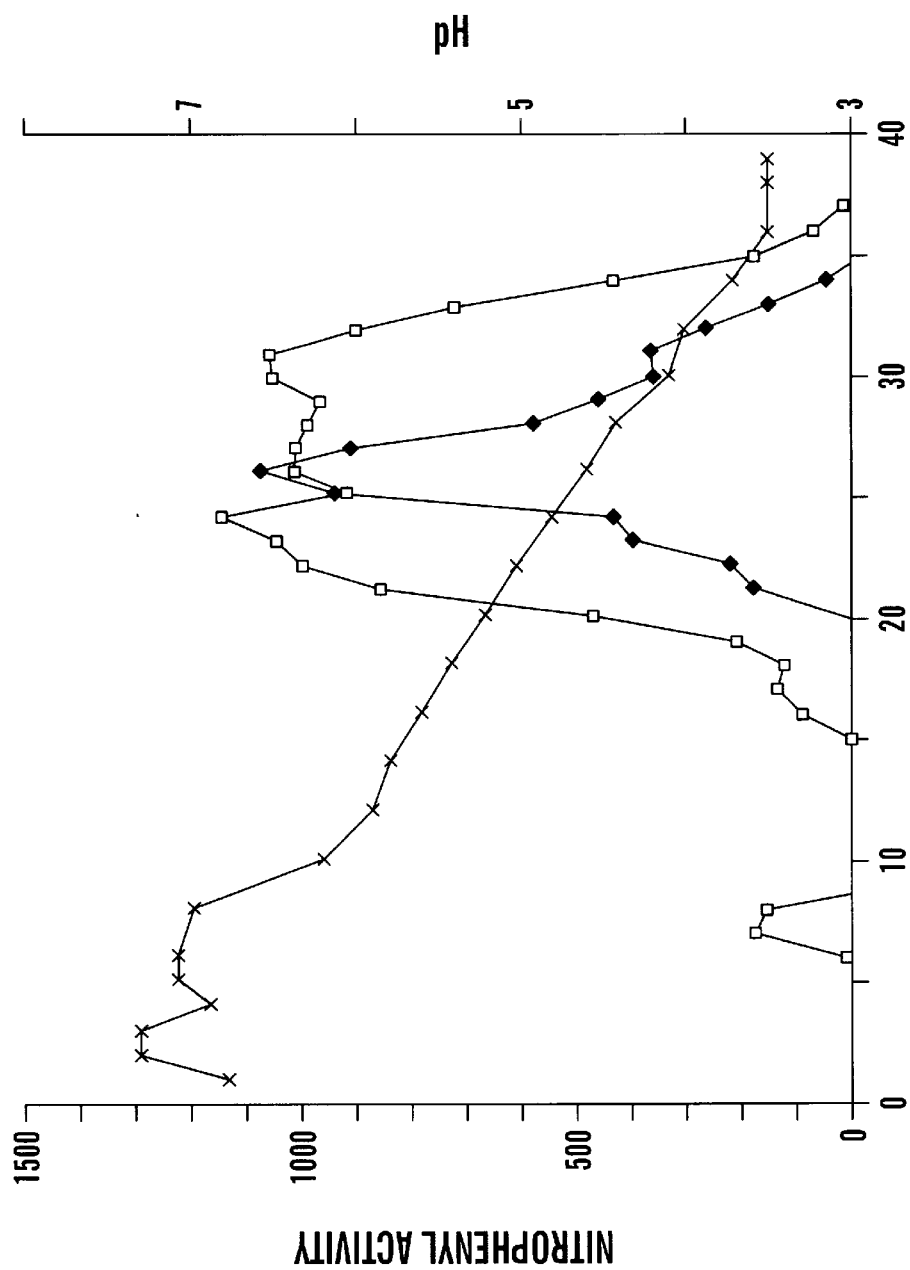
FIG. 6 depicts the elution pattern for the fractions of Set II of Example IV and provides a graph of nagase activity (Fraction vs. Nitrophenyl activity) denoted by open squares, a graph of chitobiase activity (Fraction vs. Nitrophenyl activity) denoted by filled in diamonds, and a graph of Fraction vs. pH denoted by x's.
Figure 7:
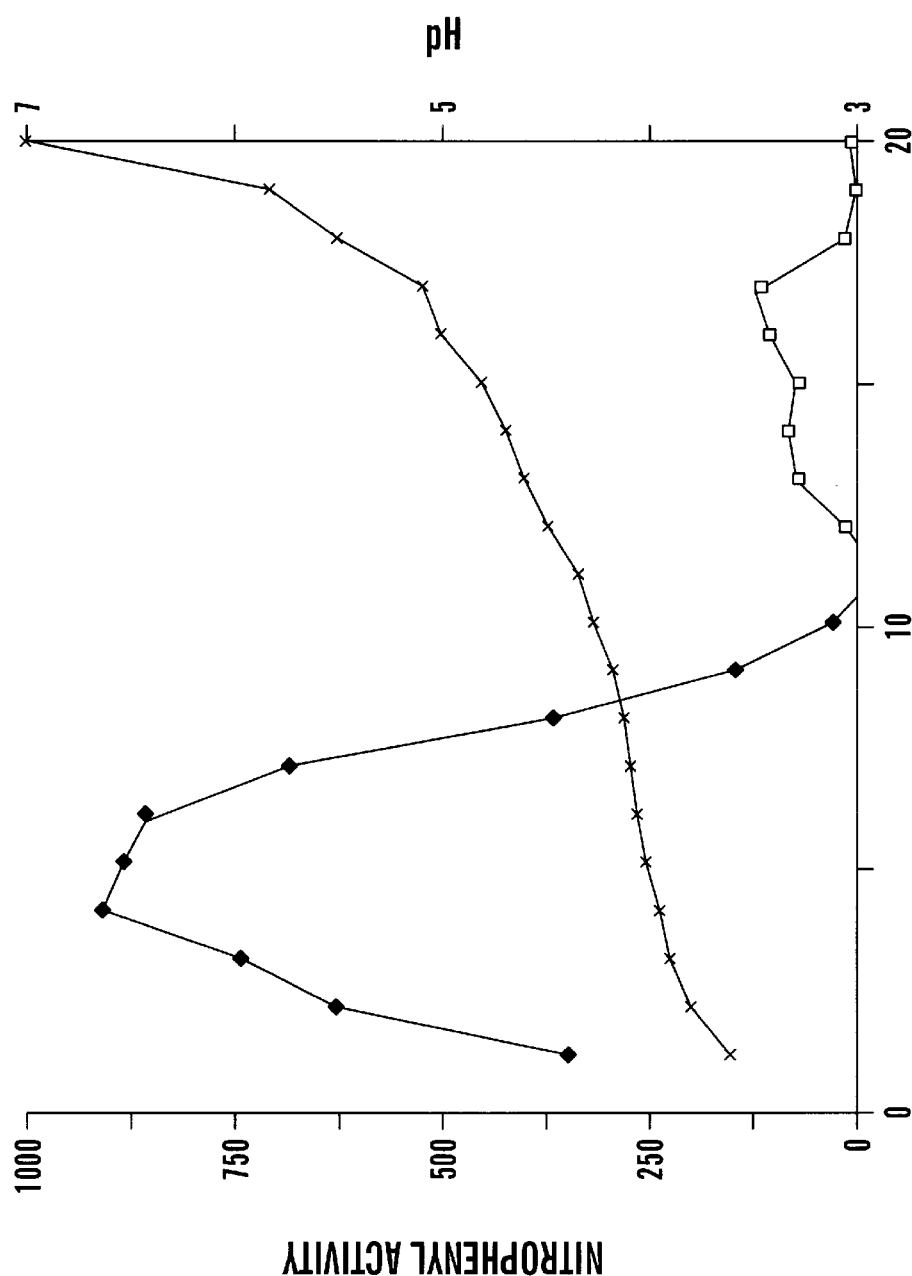
FIG. 7 depicts the elution pattern for selected fractions from chromatofocusing separation of Set II, separated according to isoelectric point on a Rotofor apparatus and provides a graph of chitobiase activity (Fraction vs. Nitrophenyl activity) denoted by filled-in diamonds, a graph of nagase activity (Fraction vs. Nitrophenyl activity) denoted by open squares and a graph of Fraction vs. pH denoted by x's. The graph shown is based upon 1.5 μl of enzyme rather than the usual 30 μl since the enzyme activity was high.

The fractions of Set II (92 ml) were pooled, and the combined fractions were concentrated in dialysis tubing immersed in polyethylene glycol (molecular weight of 35000) to approximately 25 ml and then dialyzed overnight against approximately a 10-fold volume of 25 mM imidazole-HCl buffer pH7. The concentrate was applied to a 1×30 cm chromatofocusing column packed with PBE94 (Pharmacia LKB Biotechnology) equibrated with 25 mM imidazole buffer. The proteins were eluted with Polybuffer (Pharmacia LKB Biotechnology), at a pH range of 7 to 4. The elution pattern for the concentrated fractions of set II is shown in FIG. 6. In FIG. 6, the filled in diamonds denote chitobiase activity, the open boxes denote nagase activity and the x's denote pH. In addition to chitobiase and nagase activity, a small overlapping peak of glucanase activity was detected by hydrolysis of nitrophenyl-$\beta$-D-glucopyranoside. Since the glucanase activity eluted in fractions after 28, fractions 25 to 27 were pooled for further purification. The pooled fractions were further purified by separation according to isoelectric point on a Rotofor apparatus (Bio-Rad Laboratories) employing Bio-Lyte 3/5 ampholyte at 10% v/v of the total volume and collecting peak fractions and purifying these on the Rotofor apparatus. The separation pattern for samples collected from the Rotofor apparatus is shown in FIG. 7. In FIG. 7 the filled-in diamonds denote chitobiase activity, the open boxes denote nagase activity and the x's denote pH. Fractions 2 to 8 were collected and contained chitobiase activity and no endochitinase or nagase activity. The chitobiase was determined to consist of two closely spaced protein bands on sodium dodecyl sulfate, isoelectric focusing and native gels. The larger of the two bands provided a more intensively staining protein band and was the major product. These bands correspond to activity bands as determined by overlay of fluorescent enzyme-specific substrate on isoelectric focusing and native gels. The chitobiase of the major band was determined to have a molecular weight of 40 kDa (as determined by sodium dodecyl sulfate polyacrylamide gel electrophoresis after the protein was prepared under reducing conditions, from regression based on the log of the molecular weight of standard proteins) and an isoelectric point of 3.9 as determined by isoelectric focusing electrophoresis from a regression of distance versus isoelectric point of standard proteins. The chitobiase of the minor band was determined to have a molecular weight of 36 kDa (as determined by sodium dodecyl sulfate polyacrylamide gel electrophoresis after the protein was prepared under reducing conditions, from regression based on the log of the molecular weight of standard proteins) and an isoelectric point of 3.9 as determined by isoelectric focusing electrophoresis from a regression of distance versus isoelectric point of standard proteins. The chitobiase of the minor band was present at a level of no more than 40% by weight (total chitobiase basis).

In runs where the purification step was carried out over a period of several weeks or where the purified chitobiase sample was dried in a Speedvac vacuum drying apparatus, the minor band was not present and essentially pure chitobiase of the major band was obtained.

Specific activities of the chitobiase were determined at various stages of processing with the following results.

TABLE 2

| Purification step | Specific activity (nkat/mg protein) | Recovery (%) |
|---|---|---|
| Culture filtrate | 0.54 | 100 |
| After dialysis and concentration | 12.3 | 39 |
| Set II after Sephacryl chromatography | 26.2 | 29 |
| After chromatofocusing | 51.7 | 13 |
| After isoelectric focusing in the Rotofor (major band protein) | 127 | 12 |

The above results show that the activity of the chitobiase of the major band is purified more than 75 times after chromatofocusing and more than 200 times after isoelectric focusing in the Rotofor.

The chitobiase of the major band was determined to have an optimum activity between pH 4 and pH 7.

EXAMPLE V

The essentially pure endochitinase of Example IV and essentially pure chitobiase of the major band of Example IV and a 1:1 (w/w) mixture thereof were assayed for antifungal activity against Botrytis cinerea, Fusarium solani, Ustilago avenae, Uncinula necator, Trichoderma harzianum (ATCC 20847), Saccharomyces cerevisiae, Fusarium graminearum, Trichoderma harzianum strain P1 (ATCC 74058) and Pythium ultimum strain P4. This was carried out as follows: Equal volumes (100 µl) of fungus suspension ($10^6$ spores or cells/ml), medium and enzyme test solution of various amounts of dialyzed dried fraction in distilled water sterilized by filtration, were mixed. The medium in all cases except for Ustilago avenae was 3×potato dextrose broth (Difco Laboratories). In the case of Ustilago avenae the medium was a 3× concentration of Koller and Wubben medium, i.e., a medium containing 50 mM 2-(N-morpholino)ethanesulfonic acid containing (g/l) dipotassium hydrogen phosphate, 1.0; magnesium sulfate, 0.5; ammonium nitrate, 1.0; potassium chloride, 0.5; ferrous ammonium sulfate, 0.1; glucose, 10.0; yeast extract 1.0; and 0.5 ml of a micronutrient solution (which contained (mg/liter) sodium tetraborate decahydrate, 1500; manganese sulfate monohydrate, 15; zinc sulfate heptahydrate, 2500; cuprous sulfate pentahydrate, 100; sodium molybdate, 1000) wherein the medium was adjusted to pH 6.1 and sterilized by filtration. The assay mixtures were incubated for 22–48 hours at 20–25° C.

The results are given in the following Table 3 where "ge/re" stands for spore germination or sporidia or cell replication and "elong" stands for germ tube elongation and $ED_{50}$ means the dose for 50% inhibition of spore germination or sporidia or cell replication in the case of ge/re and 50% reduction in the length of germ tubes produced from surviving conidia as compared to length of control germ tubes (produced without enzymes present) and "n.d." stands for not determined and "chitob+endoc" stands for the 1:1 mixture of chitobiase and endochitinase.

TABLE 3

| | $ED_{50}$ for enzymes ($\mu g \times ml^{-1}$) | | | | | |
|---|---|---|---|---|---|---|
| | chitobiase | | endochitinase | | chitob + endoc | |
| FUNGI | ge/re | elong | ge/re | elong | ge/re | elong |
| Botrytis cinerea | 152 | 125 | 41 | 58 | 10 | 24 |
| Fusarium solani | 165 | 168 | 110 | 67 | 30 | 28 |
| Ustilago avenae | 179 | — | 135 | — | 34 | — |
| Uncinula necator | 180 | 173 | 35 | 30 | 13 | 10 |
| Trichoderma harzianum | 62 | 162 | 90 | 35 | n.d. | n.d. |
| Saccharomyces cerevisiae | 490 | — | 535 | — | 400 | — |
| Fusarium graminearum | 125 | 132 | 100 | 70 | n.d. | n.d. |
| Trichoderma harzianum (P1) | >1000 | >1000 | >1000 | >1000 | >1000 | >1000 |
| Pythium ultimum | >1000 | >1000 | >1000 | >1000 | >1000 | >1000 |

EXAMPLE VI

The synergy between the essentially pure endochitinase of Example IV and the essentially pure chitobiase of the major band of Example IV is demonstrated according to the formula in Richter, D. L., Pestic. Sci. 19:309–315, 1987. In accordance with that formula, if synergism exists $E_O(xA+yB) > E_O(x+y)A$, and $> E_O(x+y)B$, where $E_O$ stands for percentage inhibition and x is the concentration of A (endochitinase herein) in the enzyme mixture and y is the concentration of B (chitobiase herein) in the enzyme mixture. In this Example, assays were carried out as in Example V except that 50 μg/ml of endochitinase was used in one case and 50 μg/ml of chitobiase was used in another case and 50 μg of a 1:1 mixture of endochitinase was used in the third case and percent inhibition was determined. Since the total enzyme concentration was the same in the three cases, synergism exists according to the formula in Richter if the percent inhibition for the mixture is greater than that for either of the individual cases.

The data obtained is set forth in Table 4 below.

TABLE 4

| | enzyme(s) (total concentration = 50 μg/ml) | | |
|---|---|---|---|
| Fungus | endochitinase ($E_O$ = % inhibition) | chitobiase ($E_O$ = % inhibition) | endochitinase + chitobiase ($E_O$ = % inhibition) |
| Botrytis cinerea | 60 | 20 | 97 |
| Fusarium solani | 20 | 12.5 | 70 |
| Uncinula necator | 72 | 12 | 93 |
| Ustilago avenae | 7.5 | 5.5 | 55 |

As indicated by the data, not only is synergism present according to the formula of Richter since the percent inhibition of the mixture is greater than the percent inhibition for the same total concentration of either of the components of the mixture but also the percent inhibition for the mixture exceeds that of the sum of the percent inhibitions for the same total concentrations of the individual components.

EXAMPLE VII

Figure 8:
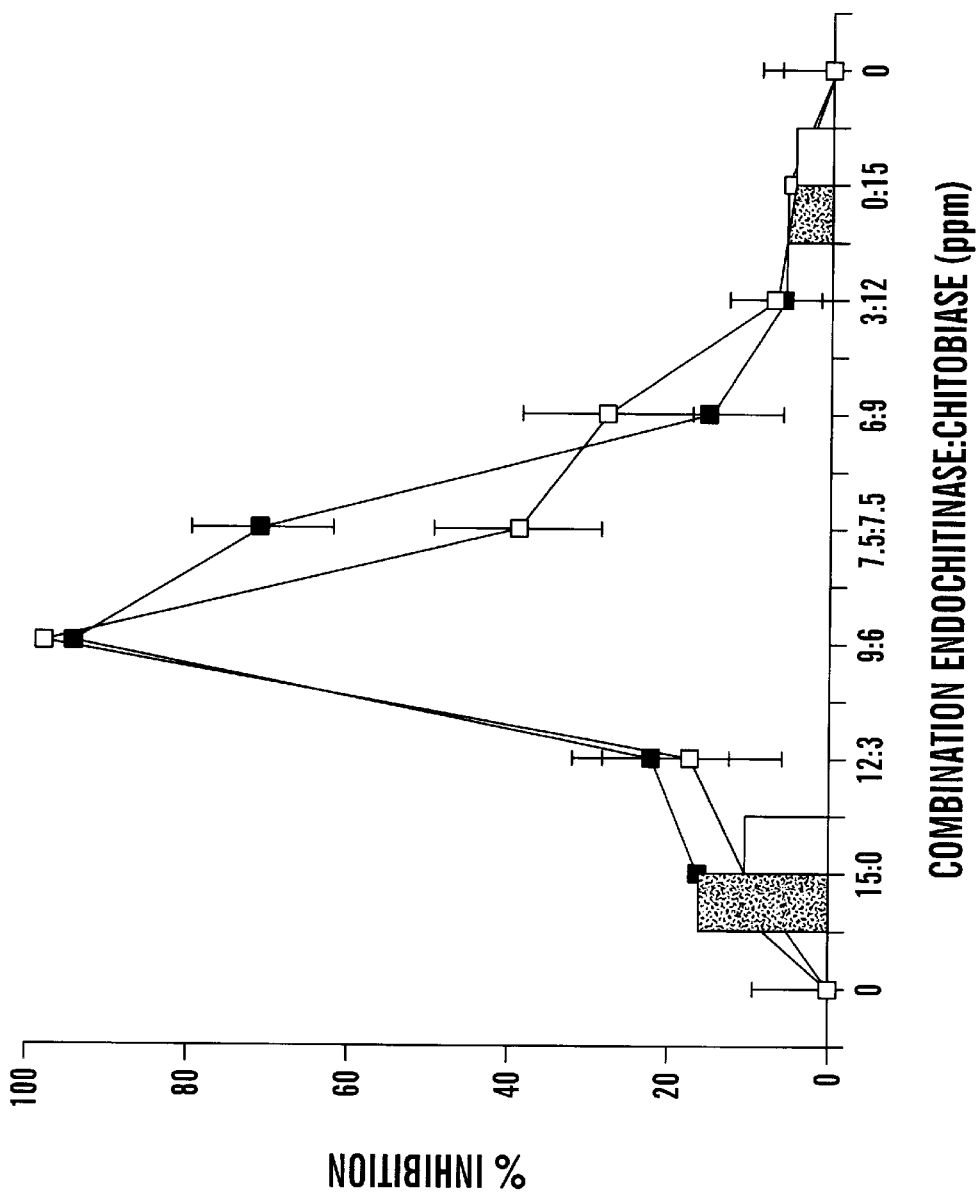
FIG. 8 depicts the synergy obtained with various combinations of endochitinase and chitobiase and shows results of Example VII.

Various combinations of the essentially pure endochitinase of Example IV and the essentially pure chitobiase of the major band of Example IV (weight ratios of 12:3, 9:6, 7.5:7.5, 6:9 and 3:12) were assayed for antifungal activity against Botrytis cinerea. Equal volumes (100 μl) of spore suspension ($10^6$/ml), 3× potato dextrose broth medium and enzyme test solution (15 ppm of enzyme combination), in distilled water, sterilized by filtration, were mixed. The assay mixtures were incubated at 25° C. for 4 hours. The results are set forth in FIG. 8 where the graph delineated by filled in blocks relates to % inhibition of spore germination and the graph delineated by open blocks relates to percent inhibition of hyphal elongation. In FIG. 8 the data at 15:0 and 0:15 is represented by bars where the solid bars represent percent inhibition of spore germination and the open bars represent percent inhibition of hyphal elongation.

EXAMPLE VIII

The gene for the endochitinase herein was isolated as follows:

I. Isolation of Messenger Ribonucleic Acid (mRNA)

Biomass of induced Trichoderma harzianum strain P1 was aseptically harvested in a sterile Buchner funnel lined with Miracloth (Calbiochem, La Jolla, Calif.) and washed with RNase-free water. The biomass was placed in a sterile disposable petri plate then quick-frozen by placing the plate in liquid nitrogen. The frozen biomass was dried by placing it in a prechilled lyophilizer and establishing a vacuum. The shelf temperature of the lyophilizer was maintained at −5° C. while the condenser temperature was set at −50° C.

Approximately 1 gram of lyophilized mycelium was resuspended in 20 ml of a guanidinium solution (5 M guanidinium thiocyanate; 50 mM Tris-HCl, pH 7.5; 10 mM $Na_2$ EDTA; 5% B-mercaptoethanol, added after the aforementioned solution had been sterilely filtered and just before use) and incubated at room temperature for 10 minutes. The supernatant was removed by centrifuging at 12,000×g for 10 minutes at 12° C. N-lauroylsarcosine was added to a final concentration of 2% and the mixture was incubated at 65° C. for 2 minutes. The aqueous phase was extracted with an equal volume of phenol/chloroform/isoamyl alcohol (25:24:1), then with an equal volume of chloroform/isoamyl alcohol (24:1). Sodium acetate was added to a final concentration of 300 mM and the RNA precipitated by the addition of 2.5 volumes of cold ethanol. mRNA was purified by direct affinity absorption to oligo dT cellulose resin using the FastTrack mRNA Isolation Kit (Invitrogen; San Diego, Calif.). This procedure yielded about 15 μg of poly $A^+$ mRNA.

II. Insertion of cloned 2'-Deoxyribonucleic Acid (cDNA) into a Bacteriophage Expression Vector, λgtII About 5 μg of poly $A^+$ RNA was used for first strand cDNA synthesis using an oligo dT primer and reverse transcriptase. The mRNA-cDNA hybrid was converted into double-stranded cDNA by the addition of RNase H, DNA polymerase I and E. coli DNA ligase. The newly formed double-stranded cDNA molecules was blunt-ended with T4 DNA polymerase and EcoR I (Not I) adaptors were added using T4 DNA ligase. Overhang ends of the adaptors were phosphorylated with T4 polynucleotide kinase. The adapted cDNAs were selected by electroelution from agarose to provide molecules ranging in size from 900 base-pairs (bp) to 7,000 bp, then ligated into lambda vector arms that had been EcoR I cut and dephosphorylated. The viral vector was encapsulated in a protein coat with approximately 60% of the vector containing a foreign insert in a total of $1.3 \times 10^5$ viral particles.

III. Production of Polyclonal Antibodies Specific for Endochitinase from T. harzianum, Strain P1

Two, eight week old female Flemish giant/Chinchilla rabbits were subcutaneously injected each week, with about 25 μg of pure endochitinase per injection, for a total of six weeks. Total immunoglobulins (Ig), containing polyclonals specific for the endochitinase, were recovered from rabbit serum by precipitation following addition of ammonium sulfate (50% of saturation) of the rabbit serum. Specificity for endochitinase was determined using ELISA and Western blotting. The two screening techniques demonstrated that the antibody that was specific for pure endochitinase was IgG. An E. coli lysate, at a 1:10 dilution, was added to the IgG solution and the mixture was incubated overnight at 4° C. and diluted 1:400 before being used to screen the cDNA library of T. harzianum strain P1.

IV. Screening the cDNA Library

A culture of E. coli, strain Y1090, was mixed with the phage particles which resulted in lytic infection, poured into a plate and incubated until viral plaques developed. The plate was overlain with a nitrocellulose membrane, that had been soaked in a solution of isopropyl-β-D-thiogalactopyranoside (IPTG) and allowed to air dry. The membrane position on the plate was marked, then carefully removed and blocked with 1% bovine serum albumin in TBS (20 mM Tris-HCl, pH 7.4: 150 mM NaCl). The membrane was probed with the polyclonal antibody solution, then washed (3x) in TBS containing 0.05% Tween-20 (TBST). Plaques expressing fusion proteins with affinity for the polyclonal antibodies were detected by hybridization to a goat antirabbit IgG (1:5000 dilution in TBS of the monovalent immunoglobulin that has a conjugated alkaline phosphatase enzyme). The membrane was washed (3x) in TBST, then developed in an alkaline phosphatase buffer (100 mM Tris, pH 9.5, 100 mM NaCl, 50 mM $MgCl_2$ containing 225 μg 4-nitro blue tetrazolium chloride and 150 μg 5-bromo-4-chloro-3-indolyl-phosphate per ml of buffer). Those viral plaques expressing the protein of interest were further purified, then stored.

V. Assaying for Enzymatically Active Fusion Protein

Enzyme assays were performed with fusion proteins, produced by the purified plaques to see if they were active. Lysogens were formed in *E. coli*, Y1089, with active fusion protein observed in polyacrylamide gels overlain with 4-methylumbelliferyl β-D-N",N"-triacetylchitotriose.

VI. Isolation of Bacteriophage Particles

Bacteriophage particles with affinity for the polyclonal antibody were isolated from lytically infected *E. coli* strain Y1090. Lytically infected bacterial cells were plated on LB agar and after plaques developed, about 6 ml of SM medium (50 mM Tris-HCl pH 7.5, 100 mM NaCl, 10 mM $MgSO_4$, 0.01% gelatin) was added to the plate, which was placed on a rotary shaker at 4° C. After an overnight incubation, the liquid was removed and chloroform (7% final concentration) was mixed into the liquid, with the upper aqueous phase removed by centrifugation. DNase and RNase (final concentration of 1 μg/ml of each enzyme) were added and the mixture shaken at 37° C. for 1 hr. Chloroform (7%) was again added, the mixture was centrifuged, and the aqueous phase containing the phage particles recovered. The phage particles were ready for storage in 1% chloroform or for isolation of DNA. The phage particles constitute λgtll recombinant containing a cDNA fragment of the gene encoding for the endochitinase herein and a sample in TE buffer (100 mM Tris-HCl, pH 7.6,+1 mM EDTA) was deposited with the American Type Culture Collection, 12301 Parklawn Drive, Rockville, Md. 20852, on Jul. 6, 1992, under the terms of the Budapest Treaty and has been assigned accession number ATCC 55338.

VII. Isolation of Viral DNA

NaCl was added to suspension of bacteriophage particles to give a 1 M solution and incubated 1 hr in an ice bath. The mixture was centrifuged at 11,000xg for 10 min at 4° C. to remove cellular debris, and the supernatant recovered. Polyethylene glycol (MW 8000) was added to give a final concentration of 10% (w/v), and the mixture placed in an ice bath for 1 hr. The bacteriophage particles were recovered by centrifugation at 11,000xg for 10 min at 4° C., and the supernatant removed and discarded. The bacteriophage particles were resuspended in SM medium, an equal volume of chloroform was added, mixed, centrifuged and the aqueous phase retained. The bacteriophage particles were recovered by centrifugation at 25,000xg for 2 hr at 4° C. SM medium (1 to 2 ml) was added and the mixture was incubated at 4° C. with shaking. Proteinase K (50 μg/ml) and sodium dodecyl sulfate (final concentration 0.5% from a 20% stock solution) were added and mixed by inverting the mixture several times in a closed tube. The mixture was incubated at 50° C. for 1 hr, cooled to room temperature and an equal volume of buffer-equilibrated phenol was added. The tube was inverted several times to mix, the phases were separated by centrifugation and the upper phase recovered by gentle suction with a wide-bore pipet. The aqueous phase was extracted with an equal volume of phenol/chloroform/isoamyl alcohol (25:24:1), then with an equal volume of chloroform/isoamyl alcohol (24:1). Sodium acetate was added to a final concentration of 300 mM and the DNA precipitated by the addition of 2.5 volumes of cold ethanol.

VIII. Removal of the cDNA Insert

The foreign DNA was recovered from the DNA purified from λgtll by digestion with Not I. only adaptors on either side of the cDNA were cut, with nucleotide sequence comprising fragment of the gene coding for endochitinase released in an undigested state. The released segment was estimated to be 1150 base pairs in length, based on estimations of size versus that of standards following electrophoretic separations.

IX. Obtaining the Sequence of the Gene

When the released segment was sequenced, it was found to be 1095 base pairs long, including 8 base pairs at the 5' end that derive from λgtll and 13 base pairs in the poly A tail. It also contained 209 base pairs at the 3' end which did not code for amino acids, so the released segment was not of sufficient length to code for the entire amino acid sequence of a 40 kDa protein. Moreover, the segment contained no ATG start codon, or other indication of a start to the gene. Therefore, it was concluded that the segment was missing a portion at the 5' end of the gene. The sequence of the 1074 base pairs of the segment corresponding to portion at the 3' end of the gene, i.e., of fragment at the 3' end of the gene excluding the 13 base pairs of the poly A tail, is set forth in the Sequence Listing as SEQ ID NO:3. Sequencing was carried out by the Sanger (dideoxy) method.

A 20 base pair primer consisting of base pairs 70 through 89 downstream from the 5' end of the fragment having the sequence set forth in the Sequence Listing as SEQ ID NO:3, is set forth in the Sequence Listing as SEQ ID NO:4. This 20 base pair primer is designated hereinafter as the nested primer. The nested primer was used in combination with forward or reverse λgtll primers. Small aliquots from the cDNA library ($10^5$ phage) were amplified by lytic infection of *E. coli* Y1090 and subjected to polymerase chain reaction in λgtll that contained both the nested primer and either the forward or reverse λgtll primers. Any amplified segment coding for the remainder of the gene would contain at its 3' end the first 89 base pairs of the 5' end of the original gene fragment, plus the remainder of the gene. Moreover, there is a Pst I restriction site 15 base pairs from the 5' end of the original gene fragment so digestion of the proper amplified segment with Pst I would provide a 74 base pair segment.

Following amplification, several segments were obtained, including a 628 base pair fragment that appeared with both nested and forward or nested and reverse primers. This is expected since the intact gene likely would have inserted in both orientations into λgtll. When digested with Pst I, this fragment gave the expected 74 base pair segment. Therefore, the 628 base pair portion was ligated into pCRII (TA cloning kit, Invitrogen) and sequenced by the Sanger (dideoxy) method. The sequence is set forth in the sequence listing as SEQ ID NO:5. The first 59 base pairs of this 628 base pair fragment arose from λgtll since the reverse primer was 59 base pairs from the insertion point in the vector. The 89 base pair overlap region was identical between the original 1074 base pair fragment and the 628 base pair product. Thus, the sequence of the entire gene is indicated from the isolated fragments. The sequence of the entire gene is 1554 base pairs long excluding the 13 base pairs in the poly A tail and the λgtll sequence at the 5' end of the 628 base pair fragment and this 1554 base pair sequence is set forth in the Sequence Listing as SEQ ID NO:1. The overlap region referred to is at positions 481–569. The entire sequence includes a 73 base pair untranslated leader sequence, an open reading frame encoding a putative protein of 424 amino acids and 209 base pair untranslated 3' region. The sequence of the protein is set forth as a feature in SEQ ID NO:1 and is also set forth in SEQ ID NO:2. The 424 amino acid protein includes a 35 amino acid leader sequence that must be cleaved to give rise to a mature protein of 389 amino acids. The 35 amino acid leader sequence has many characteristics of a signal peptide including a core of hydrophobic amino acids. The amino acid sequence deduced for the mature protein provides a mass of 42.66 kDa and has an isoelectric point of 4.53, which are reasonably close to the values of 40 kDa and 3.9 estimated from gel electrophoresis of the isolated protein; the slight variations may result from secondary modifications of the protein, e.g., low levels of carbohydrates attached to the protein.

X. Isolating the Gene

A 20 base pair primer consisting of base pairs 1520 through 1539 of the gene was prepared. It has the sequence set forth in the Sequence Listing as SEQ ID NO:6. This primer was used together with a reverse λgtll primer to screen aliquots of the cDNA library in λgtll, and an aliquot that gave a 1550 base pair band upon electrophoresis (on gels, bands differing in fewer than about 50 base pairs cannot be distinguished in nucleotides of this size). Performance of a Southern blot on the gel and probing with an 81 base pair fragment labeled with digoxigenin (Boehringer Mannheim, Mannheim, Germany) made up of bases 489–569 verified that this band was homologous with the probe and that the entire gene is contained in λgtll clone. The appropriate clone is purified by excising the plaque giving the positive reaction, using this to reinfect *E. coli*, again isolating and probing plaques and continuing this until all plaques are homologous with the probe. The presence of the entire gene is verified by detection of the entire sequence via amplification with polymerase chain reaction using forward and reverse λgtll primers.

EXAMPLE IX

Purified Endochitinase from *G. virens* Strain 41 (ATCC 20906)

Synthetic medium is made up containing 680 mg $KH_2PO_4$, 870 mg $K_2HPO_4$, 200 mg KCl, 1 g $NH_4NO_3$, 200 mg $CaCl_2$, 200 mg $MgSO_4.7H_2O$, 2 mg $FeSO_4$, 2 mg $ZnSO_4$, 2 mg $MnSO_4$, 42 g moist purified colloidal chitin (prepared as described in Vessey, J. C., et al, Trans. Br. Mycol. Soc. 60:710–713, 1973), 5 g sucrose, in 1 L distilled water, final pH 6.0.

100 ml of the synthetic medium is placed in a 250 ml Erlenmeyer flask.

The flask is inoculated with conidia grown by inoculation of potato dextrose agar (conidia of *Gliocladium virens* ATCC 20906) to provide $10^7$ conidia $ml^{-1}$ medium and the admixture is incubated at 25° C. for 5 or 7 days on a rotary shaker at 200 rpm. The culture filtrate is harvested by centrifugation at 8000×g for 10 minutes and removal of residual particulates by filtration through a glass fiber filter.

The purified endochitinase is isolated from the culture filtrate as described below with all steps being carried out at 4° C. except for concentration which was carried out at room temperature.

The filtered culture filtrate is transferred into dialysis tubing (6,000 to 8,000 Da cutoff) and dialyzed overnight against 50 mM potassium phosphate buffer pH 6.7 (5 L buffer $L^{-1}$ culture filtrate), and then concentrated 30–40 fold by placing the tubing in solid polyethylene glycol (35,000 MW; Fluka Chemika-Biochemica, Buchs, Switzerland). The concentrate is then applied to a gel filtration column (5×60 cm) containing Sephacryl S-300 HR (Pharmacia LKB Biotechnology, Uppsala, Sweden) equilibrated with 50 mM potassium phosphate buffer pH 6.7 containing 200 mM NaCl. The material from 1 L of culture medium is chromatographed separately in two samples on Sephacryl S-300 HR. Fractions, approximately 8 ml each, are eluted with 1500 ml of 50 mM potassium phosphate buffer containing 200 mM NaCl. A first peak between fractions 70 and 120 contains high levels of chitobiosidase and N-acetyl-β-glucosaminidase activity. A second peak with endochitinase, β-1,3-glucanase, and chitobiosidase activity is detected in fractions 120 to 140. Fractions 140 to 160 contain endochitinase activity; proteins in this region are apparently not separated on the basis of molecular weight, but adsorbed to the gel matrix since they elute at or greater than the total column volume. The fractions 140 to 160 from the first sample and similar fractions from the other, showing only endochitinase activity, are pooled. The pooled fractions (160 ml) are transferred into dialysis tubing (6,000 to 8,000 Da cut-off) and concentrated 30- to 40-fold by placing the tubing in solid polyethylene glycol (35,000 MW; Fluka Chemika-Biochemika, Buchs, Switzerland) and dialyzed overnight against a 20-fold volume of 25 mM ethanolamine-HCl buffer pH 8.7. The sample (about 25 ml) is then applied to a chromatofocusing column (1×30 cm) packed with PBE94 (Pharmacia LKB), and equilibrated with the same buffer used for dialysis. The column is eluted at a flow rate of 50 ml $h^{-1}$ with Polybuffer 96 (Pharmacia LKB) diluted 1:10 and adjusted to pH 7.0 with HCl according to the manufacturer's direction. A sharp peak at pH 8.0 containing endochitinase activity is detected in the eluted fractions. The peak fractions are pooled and the pooled fractions (about 40 ml) are dialyzed first against a 20-fold volume of 1M NaCl and then against a 40-fold volume of distilled water to remove Polybuffer, and concentrated to a volume of 2 ml in a collodion bag system (10,000 Daj UH 100/1, Schleicher & Schuell Inc., Keene, N.H.). The sample (2 ml), i.e., the concentrated fractions, are applied to compartments 15 and 16 (pH 8.0–8.5) of a Rotofor isoelectric focusing cell (Bio-Rad, Richmond, Calif.) loaded with 35 ml distilled water containing 2% of Biolyte Ampholytes pH 3–10 (Bio-Rad), run at 12 W constant power, at a temperature of 40° C., after one hour of prefocusing run, and the run is continued for 5 hours. The fractions (each about 2 ml) are collected and assayed for endochitinase activity. The peak fractions contain homogeneous endochitinase as shown by the presence of a single protein band upon SDS-PAGE and upon Native PAGE. A single fluorescent activity band is observed following overlay of the native gel with the methylumbelliferyl substrate. This activity corresponds to the position of the single protein band detected with coomassie blue and silver stain.

The peak (active) fractions are pooled, dialyzed against 1M NaCl and then against distilled water as described above, and concentrated to dryness in a Speedvac apparatus. The enzyme is stored at −20° C. and reconstituted in an appropriate volume of sterilized distilled water for use.

The endochitinase from *G. virens* strain 41 (ATCC 20906) has a molecular weight of 41 kDa as determined by sodium dodecyl sulfate polyacrylamide gel electrophoresis after the protein was prepared under reducing conditions from a regression based on the log of the molecular weight of standard proteins, and an isoelectric point of 7.8 as determined by isoelectric focusing electrophoresis from a regression of distance versus isoelectric point of standard proteins, as described in U.S. patent application Ser. No. 08/184,115.

EXAMPLE X

Antifungal Use

In this example, the endochitinase is the above-described endochitinase from Gliocladium virens strain 41 having accession No. 20906.

Assays were carried out for inhibition of the plant pathogen Botrytis cinerea as described in Lorito, M., et al, Phytopathology, Vol. 83, No. 3, 303–307 (1993) except that the spores were harvested and suspended in 5 mM sodium acetate buffer to improve spore germination, the assay was performed in flat bottomed wells in microtiter plates and observed after 24 hr. with an inverted microscope and 50 µg/ml of the antibiotic ampicillum was used to prevent bacterial growth during the assay.

Results of % inhibition of hyphal elongation are given in Table 5 below:

TABLE 5

| Enzyme(s) and Concentration(s) | % Inhibition |
| --- | --- |
| Endochitinase at 1 µg/ml | 5.5 |
| Endochitinase at 5 µg/ml | 24 |
| Endochitinase at 10 µg/ml | 54 |

Results of % inhibition of spore germination are given in Table 6 below:

TABLE 6

| Enzyme(s) and Concentration(s) | % Inhibition |
| --- | --- |
| Endochitinase at 1 µg/ml | 5.5 |
| Endochitinase at 5 µg/ml | 25 |
| Endochitinase at 10 µg/ml | 51 |

As indicated above, the term "chitobiase" is used herein to mean enzyme that cleaves dimeric unit from chitin. Others use this term to refer to an enzyme that cleaves chitobiose (the dimer) to monomeric units. So that there can be no confusion in the minds of those reading the term herein without having referred to the definition herein, the term "chitin 1,4-β-chitobiosidase" or the term "chitobiosidase" can be used in place of the term "chitobiase" herein to mean enzyme that cleaves dimeric unit from chitin.

SEQ ID NO:7 constitutes base pairs 443–487 of SEQ ID NO:1. SEQ ID NO:8 constitutes base pairs 566–595 of SEQ ID NO:1. SEQ ID NO:9 constitutes amino acids 123–138 of SEQ ID NO:2. SEQ ID NO:10 constitutes amino acids 165–174 of SEQ ID NO:2.

Variations in the invention will be obvious to those skilled in the art. Therefore, the invention is defined by the claims.

---

What is claimed is:

1. An isolated DNA molecule encoding a fungal endochitinase comprising an amino acid sequence of SEQ. ID. No. 9 or SEQ. ID. No. 10.

2. An isolated DNA molecule according to claim 1, wherein the endochitinase comprises an amino acid sequence of SEQ. ID. No. 9.

3. An isolated DNA molecule according to claim 1, wherein the endochitinase comprises an amino acid sequence of SEQ. ID. No. 10.

4. A vector containing the DNA molecule according to claim 2.

5. A vector containing the DNA molecule according to claim 3.

6. A host cell containing the DNA molecule according to claim 2.

7. A host cell containing the DNA molecule according to claim 3.

8. A host cell according to claim 6, wherein said host cell is a microorganism.

9. A host cell according to claim 7, wherein said host cell is a microorganism.

10. A host cell according to claim 6, wherein said host cell is a plant cell.

11. A host cell according to claim 7, wherein said host cell is a plant cell.

12. A transgenic plant containing the DNA molecule according to claim 2.

13. A transgenic plant containing the DNA molecule according to claim 3.

14. An isolated DNA molecule encoding an endochitinase and comprising the nucleotide sequence of SEQ. ID. No. 7 or the nucleotide sequence of SEQ. ID. No. 8.

15. An isolated DNA molecule according to claim 14 comprising the nucleotide sequence of SEQ. ID. No. 7.

16. An isolated DNA molecule according to claim 14 comprising the nucleotide sequence of SEQ. ID. No. 8.

17. A vector containing the DNA molecule according to claim 14.

18. A vector containing the DNA molecule according to claim 15.

19. A vector containing the DNA molecule according to claim 16.

20. A host cell containing the DNA molecule according to claim 14.

21. A host cell containing the DNA molecule according to claim 15.

22. A host cell containing the DNA molecule according to claim 16.

23. A host cell according to claim 20, wherein said host cell is a microorganism.

24. A host cell according to claim 20, wherein said host cell is a plant cell.

25. A transgenic plant containing the DNA molecule according to claim 14.

26. A transgenic plant containing the DNA molecule according to claim 15.

27. A transgenic plant containing the DNA molecule according to claim 16.

28. An isolated DNA molecule encoding a fungal endochitinase having an amino acid sequence comprising SEQ.ID. No. 2.

29. A vector containing the DNA molecule according to claim 28.

30. A host cell containing the DNA molecule according to claim 28.

31. A host cell according to claim 30, wherein said host cell is a microorganism.

32. A host cell according to claim 30, wherein said host cell is a plant cell.

33. A transgenic plant containing the DNA molecule according to claim 28.

* * * * *